(12) United States Patent
Silin

(10) Patent No.: US 10,086,129 B2
(45) Date of Patent: Oct. 2, 2018

(54) VALVE, IMPLANT INCLUDING THE VALVE, FLUID TRANSFER ARRANGEMENT, AND METHOD OF TREATMENT USING THE SAME

(71) Applicant: Douglas D. Silin, Cheshire, CT (US)

(72) Inventor: Douglas D. Silin, Cheshire, CT (US)

( * ) Notice: Subject to any disclaimer, the term of this patent is extended or adjusted under 35 U.S.C. 154(b) by 1197 days.

(21) Appl. No.: 14/206,813

(22) Filed: Mar. 12, 2014

(65) Prior Publication Data

US 2014/0276345 A1    Sep. 18, 2014

Related U.S. Application Data

(60) Provisional application No. 61/779,448, filed on Mar. 13, 2013.

(51) Int. Cl.
| | |
|---|---|
| *A61M 5/00* | (2006.01) |
| *A61M 1/36* | (2006.01) |
| *A61M 39/02* | (2006.01) |
| *A61M 39/22* | (2006.01) |
| *A61M 39/10* | (2006.01) |

(52) U.S. Cl.
CPC ...... *A61M 1/3655* (2013.01); *A61M 39/0208* (2013.01); *A61M 39/223* (2013.01); *A61M 2039/1072* (2013.01)

(58) Field of Classification Search
CPC ............ A61M 1/3655; A61M 39/0208; A61M 39/223; A61M 2039/1072
See application file for complete search history.

(56) References Cited

U.S. PATENT DOCUMENTS

| | | |
|---|---|---|
| 4,397,335 A | 8/1983 | Doblar et al. |
| 4,898,669 A * | 2/1990 | Tesio ................ A61M 39/0247 |
| | | 137/625.47 |
| 4,983,162 A | 1/1991 | Metais et al. |
| 6,293,922 B1 | 9/2001 | Haase |
| 6,726,711 B1 | 4/2004 | Langenbach et al. |
| 7,025,741 B2 | 4/2006 | Cull |

(Continued)

FOREIGN PATENT DOCUMENTS

WO   2011150978 A1   12/2011

OTHER PUBLICATIONS

International Search Report; International Application No. PCT/US2014/024096; Filing Date: Mar. 12, 2014; dated Jul. 14, 2014; 3 pages.

(Continued)

*Primary Examiner* — Ariana Zimbouski
(74) *Attorney, Agent, or Firm* — Cantor Colburn LLP

(57) ABSTRACT

A valve includes a housing with a cavity having at least one connector fluidically connecting the cavity to an outside of the housing and a plug that is movable within the housing. The plug is movable at least between a first position that substantially occludes fluidic communication between the cavity and an outside of the housing through the at least one connector and a second position that allows fluidic communication between the cavity and the outside of the housing through the at least one connector. The valve also includes a septum in operable communication with the housing that is sealingly penetrable by a fluid transfer device, wherein the fluid transfer device is capable of moving the plug between at least the first position and the second position.

26 Claims, 12 Drawing Sheets

(56) References Cited

U.S. PATENT DOCUMENTS

| | | |
|---|---|---|
| 7,108,673 B1 | 9/2006 | Batiste |
| 7,223,257 B2 | 5/2007 | Shubayev et al. |
| 7,347,853 B2 | 3/2008 | DiFiore et al. |
| 7,503,902 B2 | 3/2009 | Jensen et al. |
| 7,566,317 B1 | 7/2009 | Batiste et al. |
| 7,762,980 B2 | 7/2010 | Gertner |
| 7,766,853 B2 | 8/2010 | Lane |
| 7,833,186 B1 | 11/2010 | Batiste |
| 8,012,134 B2 | 9/2011 | Claude et al. |
| 8,057,421 B2 | 11/2011 | Akingba |
| 2005/0080401 A1* | 4/2005 | Peavey .............. A61M 39/0208 604/891.1 |
| 2005/0143687 A1 | 6/2005 | Rosenblatt et al. |
| 2005/0159714 A1* | 7/2005 | Gibson .............. A61M 5/14276 604/288.03 |
| 2008/0228132 A1 | 9/2008 | Langenbach |
| 2009/0030498 A1 | 1/2009 | Cull |
| 2011/0172692 A1 | 7/2011 | Wu |
| 2011/0257577 A1 | 10/2011 | Lane et al. |

OTHER PUBLICATIONS

Written Opinion of the International Searching Authority; International Application No. PCT/US2014/024096; Filing Date: Mar. 12, 2014; dated Jul. 14, 2014; 9 pages.

* cited by examiner

VALVE, IMPLANT INCLUDING THE VALVE, FLUID TRANSFER ARRANGEMENT, AND METHOD OF TREATMENT USING THE SAME

CROSS-REFERENCE TO RELATED APPLICATIONS

This application claims priority to U.S. Provisional Application No. 61/779,448, filed on Mar. 13, 2013, and all the benefits accruing therefrom, the content of which in its entirety is herein incorporated by reference.

BACKGROUND

Dialysis of a patient having renal failure can involve peritoneal dialysis or hemodialysis. In hemodialysis, blood is cyclically withdrawn from the patient, circulated through a filtration system, and returned to the patient. This requires access to the patient's circulatory system, which can be accomplished with a catheter or shunt. A dialysis shunt connects a portion of the arterial system to the venous system such that blood flows through the shunt and bypasses a section of the patient's body (e.g., a hand in the case of dialysis via the forearm) that the artery ordinarily supplies with blood. The shunt can be a fistula or graft. A fistula is a direct connection of an artery and vein, and a graft connects an artery and vein. A surgically created shunt requires time to mature before using it for dialysis. Often, the maturation time necessitates placement of a temporary dialysis method.

Decreased supply of blood to an extremity, e.g., a foot or hand, can lead to ischemia, which can create a condition such as a cold limb or, in more severe cases, tissue damage due to deprivation of oxygen, glucose, and similar compounds required for cellular metabolism. Moreover, stagnation of blood in the shunt or blood vessel can lead to thrombosis, failure of the shunt, complications including embolism, and additional surgical or interventional procedures with their inherent risks and costs.

Further, each hemodialysis session usually lasts for three to four hours and is usually performed three times per week. During the time that dialysis is not performed, a shunt has blood flowing through it. Consequently, blood may flow through the shunt greater than 90% of the time without benefit and possibly causing harm. Constant flow of blood through the shunt can cause the formation of a blockage and failure of the shunt or dialysis system. A shunt can fail due to developing such a blockage that causes blood stagnation in the shunt, in the inflow arterial system, or in the outflow venous system, with subsequent clot formation. Clotting of the shunt requires a surgical or radiological procedure, time, and expense to restore blood flow.

Hence, new materials and methods for implants should be well received in the art.

SUMMARY

Disclosed herein is a valve. The valve includes: a housing defining a cavity having at least one connector fluidically connecting the cavity to an outside of the housing; a plug that is movable within the housing at least between a first position that substantially occludes fluidic communication between the cavity and an outside of the housing through the at least one connector and a second position that allows fluidic communication between the cavity and the outside of the housing through the at least one connector; and a septum in operable communication with the housing that is sealingly penetrable by a fluid transfer device, wherein the fluid transfer device is capable of moving the plug between at least the first position and the second position.

Further disclosed herein is a fluid transfer arrangement. The arrangement includes a valve that is implantable under the skin and having a first connector and a second connector, wherein the first and second connectors are fluidically connectable to first and second blood vessels, wherein fluidic communication between the first and second blood vessels is occluded when a plug within the valve is in a first position and allowed when the plug is in a second position, wherein the plug is movable between at least the first position and the second position by a fluid transfer device, which is engagable with the valve and able to move the plug between at least the first position and the second position.

Further disclosed herein is an implant. The implant includes a valve which is implantable within a human body and which includes at least one connector, wherein the at least one connector is in operable communication with the valve, which is openable and closable to flow in response to rotation of a fluid transfer device while the fluid transfer device is engaged with the valve.

Also disclosed is a method of dialysis, the method including: locating a valve disposed within a patient; inserting a fluid transfer device in a keyway of the valve; rotating the fluid transfer device with respect to the housing of the valve to open the valve; and communicating a fluid through the fluid transfer device to perform dialysis, wherein the valve comprises a housing defining a cavity having at least one connector fluidically connecting the cavity to an outside of the housing, a plug being movable within the housing at least between a first position that substantially occludes fluidic communication between the cavity and an outside of the housing through the at least one connector and a second position that allows fluidic communication between the cavity and the outside of the housing through the at least one connector, and a septum in operable communication with the housing being sealingly penetrable by a fluid transfer device, the fluid transfer device being capable of moving the plug between at least the first position and the second position.

BRIEF DESCRIPTION OF THE DRAWINGS

The following descriptions should not be considered limiting in any way. With reference to the accompanying drawings, in which like elements are numbered alike.

DETAILED DESCRIPTION

A detailed description of one or more embodiments is presented herein by way of exemplification and not limitation.

Figure 2:
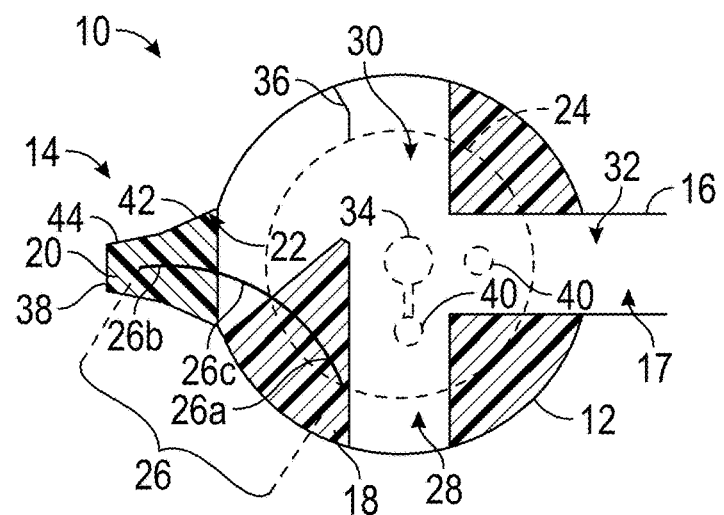
FIG. 2 shows a cross-section of the valve shown in FIG. 1 with a plug in a seat.
Figure 3:
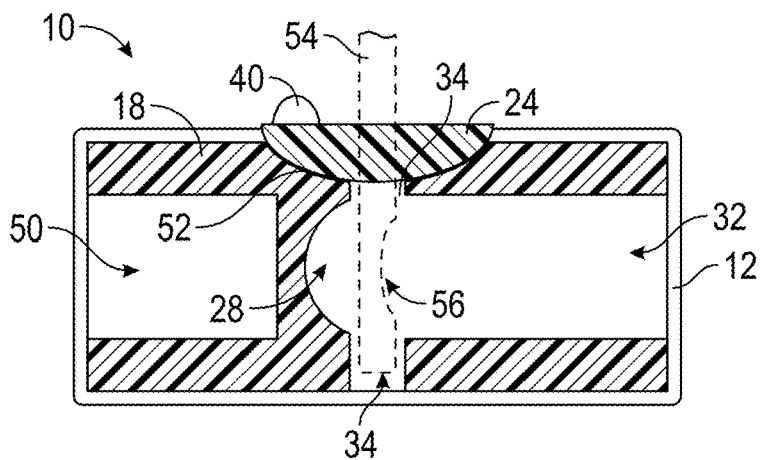
FIG. 3 shows a transverse cross-section of the valve shown in FIG. 1.
Figure 6:
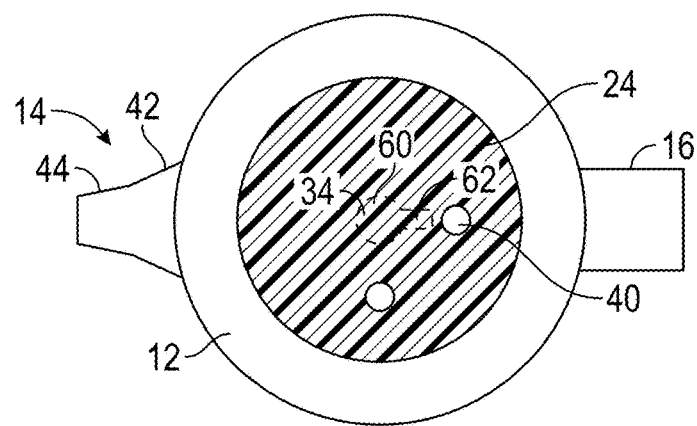
FIG. 6 shows a top view of the valve shown in FIG. 1.

Chronic exposure of the venous system to arterial pressure can produce deleterious changes in the venous system that restrict blood flow in the venous system and cause subsequent failure of arterio-venous shunts. It has been found that decreasing the amount of time that a biological fluid flows through or is present in an implant can increase the lifetime of the implant. In addition, the implant disclosed herein decreases the exposure of the implant to a source of particles, such as blood, that can build up in the implant such that a lifetime and usefulness of the implant is increased. Moreover, removing biological fluids from the implant after exposure of such fluids in the implant further increases the lifetime of the implant. Prolonging the lifetime of the implant decreases medical expenses, enhances patient comfort, and increases efficiency in treating a patient In an embodiment, the implant herein includes a valve 10, which is shown in the longitudinal cross-sections of FIGS. 1 and 2. FIGS. 3 and 6 are respectively a transverse cross-section and top view of the valve 10. The valve 10 has a first connector 14 and a second connector 16 that protrude from a housing 12 of the valve 10 and respectively connect to a first fluid flow member and second fluid flow member (not shown). A rotary member 18 and a plug 20 are disposed in the housing 12 such that the plug 20 connects to the rotary member 18. A seat 22 is arranged proximate to or disposed in the first connector 14 to sealingly receive the plug 20. A septum 24 is disposed on the housing 12. The septum 24 seals a top portion of the housing 12 and receives a fluid transfer device 54.

The first connector 14 and the second connector 16 have a fluid flow channel 17 to communicate fluid from outside of the valve 10 to an interior of the valve 10. Additionally, a primary flow channel 28 and a secondary flow channel 30 are disposed in the rotary member 18 such that the primary and secondary flow channels 28 and 30, respectively, are in fluid communication with each other and define a cavity within the housing 12 of the valve. The rotary member 18 is configured to rotate in response to application of an angular force, i.e., a torque. In an embodiment, the rotary member 18 rotates between a first position (shown in FIG. 1) and second position (shown in FIG. 2) with respect to the housing 12, with the direction of rotation depicted by arc 19 in FIG. 1. Therefore, rotary member 18 can rotate clockwise or counter-clockwise with respect to the orientation of the housing 12 in FIG. 1.

Communication of a fluid through the valve 10 can include movement of the fluid from a fluid flow member connected to the first connector 14 through the fluid flow channel 17 of the first connector 14, the secondary flow channel 30, the primary flow channel 28, and the fluid flow channel 17 of the second connector 16. Communication of the fluid through the valve 10 can be impeded in response to rotation of the rotary member 18. As used herein, impeding a communication of fluid includes completely or substantially blocking the flow of the fluid so that the flow is greatly reduced or totally interrupted. Such an interruption in fluid communication can be intermittent or continuous and depends on the orientation of the rotary member 18 and plug 20 within the housing 12.

Figure 1:
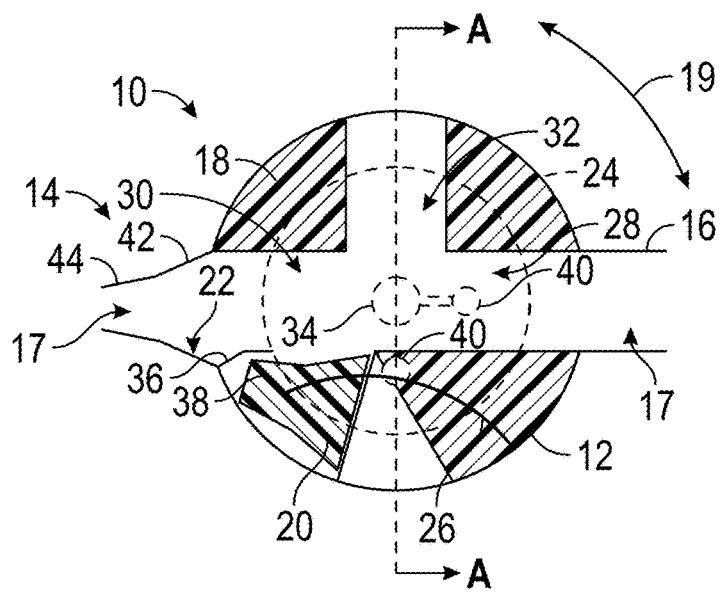
FIG. 1 shows a longitudinal cross-section of an embodiment of a valve.

According to an embodiment, a coupling 26 connects the rotary member 18 to the plug 20. The coupling 26 can be flexible and can exert an outwardly radial force on the plug 20 to urge the plug 20 into the seat 22 in response to the plug 20 being proximate to the seat 22. In this manner, as the rotary member 18 rotates, the plug 20 also rotates due to the coupling 26. With reference to FIG. 2, when the plug 20 is disposed in the seat 22, the plug 20 impedes, e.g., completely stops, the communication of fluid through the fluid flow channel 17 of the first connector 14 but still allows fluid to flow through a fluid transfer device (e.g., fluid transfer device 54 shown in FIG. 3) into a tertiary flow channel 32 and out the second connector 16. In an embodiment, the communication of fluid is stopped completely. Thus, with the rotary member 18 in the first position as shown in FIG. 1, fluid can be communicated, i.e., flow, through the valve 10 since the plug 20 is not disposed in seat 22. In response to rotation of the rotary member 18 from the first position (FIG. 1) to the second position shown in FIG. 2, the plug 20 becomes disposed in the seat 22 of the connector to impede, e.g., halt, flow into valve 10 from first connector 14 while still allowing flow into (or out of) valve 10 from a fluid transfer device and second connector 16. To avoid accumulation or growth of material, such as a clot, the plug may fill the connector leaving substantially no void volume. Thus an outer surface of the plug may be flush with an end of the outer second portion of the connector 44, as shown in FIG. 2. Here, it is contemplated that fluid communication through the valve 10 refers to fluid traversing the valve 10 from, e.g., the first connector 14 to the second connector 16. It should be appreciated that fluid can likewise be communicated in the opposite direction, i.e., from the second connector 16 to the first connector 14.

Consequently, when the rotary member 18 is in the first position, the first connector 14, the second connector 16, the primary flow channel 28, and the secondary flow channel 30 are in fluid communication. In this state, the valve 10 is configured to communicate the fluid between the first connector 14 and the second connector 16 through the primary flow channel 28 (and allow flow through a fluid transfer device). In addition, when the rotary member 18 is in the second position, the plug 20 is disposed in the seat 22 of the housing 12 and impedes, i.e., blocks, fluid from entering (or leaving) valve 10 through the first connector 14 while allowing flow through (such as into or out) of valve 10 through a fluid transfer device and second connector 16. Accordingly, the rotary member 18 via plug 20 governs whether fluid flows through valve 10 from a fluid source or reservoir connected to the first connector 14, e.g., from an arterial system to a venous system when valve 10 is implanted into a patient. In other words, with the rotary member 18 in the first position, the valve is in an "ON" state (i.e., open) with respect to fluid communication from an exterior to an interior of the valve 10 via first connector 14. Similarly, the valve 10 can be thought of as being "OFF" (i.e., closed) when the rotary member 18 is in the second position such that the plug 20 is disposed in the seat 22.

According to an embodiment, the rotary member 18 also can include a tertiary flow channel 32 in fluid communication with the primary flow channel 28 and the secondary flow channel 30. When the rotary member is in the second (e.g., closed) position, the second connector 16, the primary flow channel 28, the secondary flow channel 30, and the tertiary flow channel 32 are in fluid communication, but none of these flow channels are in fluid communication with the first connector 14 in valve 10.

Figure 4:
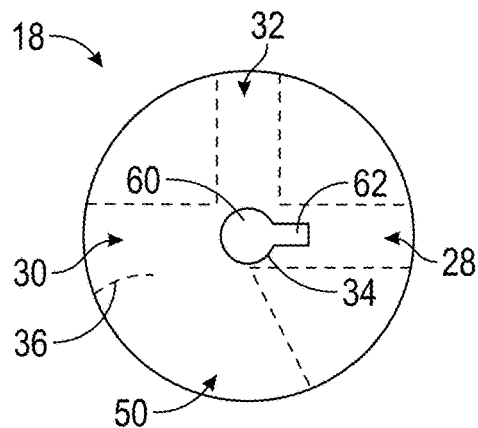
FIG. 4 shows a top view of an embodiment of a rotary member.
Figure 5:
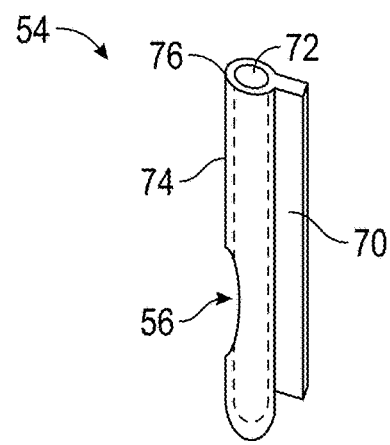
FIG. 5 shows a perspective view of an embodiment of a fluid transfer device.

FIG. 3 is a transverse cross-section taken along line A-A of the valve 10 shown in FIG. 1, and FIG. 4 is a top view of the rotary member 18. As shown in the transverse cross-section of FIG. 3 and top view of FIG. 4, the rotary member 18 of valve 10 includes a keyway 34 to engage a rotary device, e.g., a fluid transfer device 54 that provides the angular force to the rotary member 18. That is, by rotating the fluid transfer device 54 relative to the housing 12, the angular force is applied by the fluid transfer device 54 to the rotary member 18 with concomitant rotation of the rotary member 18 and plug 20. The keyway 34 can engage the fluid transfer device 54 after insertion of the fluid transfer device 54 through septum 24. In an embodiment, the keyway 34 can have a shape that matches the profile of the fluid transfer device 54. In some embodiments, the shape can be asymmetric. In another embodiment, the shape can be symmetric. The keyway 34 can include a central hole 60 and an ancillary hole 62 in which the fluid transfer device 54 fits to engage the rotary member 18 and transmit rotary motion thereto. As shown in FIG. 5, the fluid transfer device 54 can include a body 74 having a protrusion 70 extending therefrom. The body 74 inserts into the central hole 60 of the keyway 34, and the protrusion inserts into the ancillary hole 62. A bore 72 extends along a length of the body 74 to communicate fluid between the valve 10, e.g., via primary flow channel 28, and an external fluid flow system or reservoir (not shown) connected to a source end 76 of the fluid transfer device 54. Fluid communicates between the valve 10 and the fluid transfer device 54 by flowing through fluid transfer hole 56. Upon insertion of the fluid transfer device 54 through septum 24, the fluid transfer device can communicate fluid and also induce rotation of the rotary member 18 and plug 20. The fluid transfer hole 56 can be located at any suitable position of the fluid transfer device 54, e.g., on a side or at the tip of the fluid transfer device 54, and can have any suitable shape. It is contemplated that the shape and cross-sectional area of the fluid transfer hole 56 can affect a rate of fluid communication through fluid transfer device 54. The fluid transfer device 54 and protrusion 70 can have any suitable cross-sectional shape. The protrusion 70 can be disposed at any suitable location along the fluid transfer device to engage the keyway 34 of the rotary member 18.

Furthermore, since the plug 20 impedes fluid communication between the first connection 14 and the flow channels (the primary flow channel 28, the secondary flow channel 30 or the tertiary flow channel 32, indicated as dotted lines in FIG. 4) of the rotary member 18 in the second position but allows fluid communication therebetween in the first position, rotation of the fluid transfer device 54 determines whether fluid is communicated through the valve 10 from a fluid source connected to the first connector 14 as well as communicating fluid between the interior of the valve 10 (from the primary flow channel 28) and the external fluid flow system or reservoir connected to the source end 76 of the fluid transfer device 54.

According to an embodiment, the rotary member 18 further includes a plug channel 50 as shown in FIG. 3. As the plug 20 moves in response to rotation of the rotary member 18, the plug 20 traverses the plug channel 50. That is, plug 20 moves from being disposed within a perimeter of the rotary member 18 in the first position as shown in FIG. 1, to being disposed in the seat 22 in the second position as shown in FIG. 2, which is external to the rotary member 18. The motion of the plug 20 is coupled to that of the rotary member 18 by coupling 26. As show in FIG. 2, the coupling 26 includes a first end 26a attached to the rotary member 18, a second end 26b attached to the plug 20, and an intermediate portion 26c interposed between the first end 26a and the second end 26b such that the intermediate portion 26c is disposed in the plug channel 50. Rotation of the rotary member 18 is transmitted via the coupling 26 to the plug 20. In an embodiment, the first end 26a can be attached to a surface of the rotary member 18 or disposed inside a bulk of the rotary member 18 so that the material of the rotary member 18 surrounds the first end 26a. Similarly, the second end 26b can be attached to a surface of the plug or disposed inside a bulk of the plug 20 so that the material of the plug 20 surrounds the second end 26b.

Again, with reference to FIGS. 1 and 2, the rotary member 18 can include a baffle 36. The baffle 36 can extend from a periphery of the rotary member 18 into an interior portion of the rotary member 18 and can rotate freely of the housing 12. As fluid communicates from the first connector 14 to the second connector 16, the baffle 36 obstructs contact between the plug 20 and a flow of the fluid between the first connector 14 and the second connector 16. In this manner, the plug 20 does not disrupt the fluid flow, particularly by a terminus 38 of the plug 20. The baffle 36 can decrease turbulent flow of the fluid from a source connected to the first connector 14 through the valve 10.

As shown by dotted lines in FIGS. 1 and 2 and continuous lines in FIGS. 3 and 6, a septum 24 is disposed on the housing 12. In addition to accepting the fluid transfer device 54, the septum 24 may comprise a position indicator 40 disposed on a surface opposing the rotary member 18. The position indicator 40 can protrude from the surface of the septum 24. The position indicator 40 allows for determination of the orientation of the valve 10 and the relative positions of the first connector 14 and second connector 16. Additionally, a distribution of a plurality of position indicators 40 together with the shape of the keyway 34 allows tactile determination of the angular orientation of the rotary member 18 in the housing 12. In an embodiment, an alignment between the position indicator 40 proximate to second connector 16 and the protrusion 70 of the fluid transfer device 54 disposed in the ancillary hole 62 of the keyway 34 indicates that the rotary member 18 is in the first position (as in FIG. 1) such that fluid can communicate through the valve 10 between the first connector 14 and the second connector 16. Alternatively, alignment between the position indicator 40 distal to second connector 16 and the protrusion 70 of the fluid transfer device 54 disposed in the ancillary hole 62 of the keyway 34 indicates that the rotary member 18 is in the second position (as in FIG. 2) such that fluid communication is impeded through the valve 10 between the first connector 14 and the second connector 16.

Although two position indicators are shown in FIG. 6, it is contemplated that one or more position indicators 40, specifically 1 to 3 position indicators, more specifically 3 position indicators, can be present on septum 24. Further, the position indicator 40 can be a divot instead of a projection on the surface of the septum 24. An angle between the plurality of position indicators 40 can be any suitable angle, wherein this angle is with respect to the position indicators 40 and a center of the septum 24. Moreover, a linear array of position indicators, e.g., a linear arrangement of 1 to 5 position indicators, can be radially aligned with respect to the center of the septum 24. The position indicator 40 can have any suitable shape and height from the surface of the septum 24. As shown in FIG. 6, in an embodiment the position indicator can have a circular cross-section.

The septum 24 is configured to seal around the fluid transfer device 54 in response to insertion of the fluid transfer device 54 through the septum 24. The septum 24 also impedes fluid communication between an interior and exterior of the valve 10. That is, the septum 24 provides a seal for the housing 12 so that fluid does not leak from the housing 12 after insertion or removal of fluid transfer device 54 from the septum 24.

In an embodiment, the valve 10 includes a guide 52 for insertion of the fluid transfer device 54 into the rotary member 18. As shown in FIG. 3, the guide can be a contoured surface of the rotary member 18. After insertion of the fluid transfer device 54 through septum 24, the fluid transfer device 54 will be incident at the guide 52. The guide 52 aids in directing the fluid transfer device 54 into the keyway 34 of the rotary member 18. The shape of the guide 52 can be any suitable shape including a concave shape (as in FIG. 3), a V-shape, a cylindrical shape, or a stepped shape. In an embodiment, the guide 52 and the surface of the septum 24 facing the rotary member 18 have complementary shapes such that the septum 24 is maintained in sealing contact with the housing 12 and allows free rotation of the rotary member 18 in the housing 12. The septum 24 seals the housing 12 to avoid fluid leakage between the internal flow channels (e.g., between primary flow channel 28, secondary flow channel 30, and tertiary flow channel 32) of the valve 10 and the environment surrounding the valve 10. In an embodiment, the septum 24 is attached or coupled to the housing 12 so that the septum 24 remains in the same position relative to the housing 12 as the rotary member 18 rotates. In an embodiment, the septum 24 can be attached or coupled to the rotary member 18 so that they rotate together with the septum 24 providing a seal between the rotary member 18 and the housing 12.

Figure 7A:
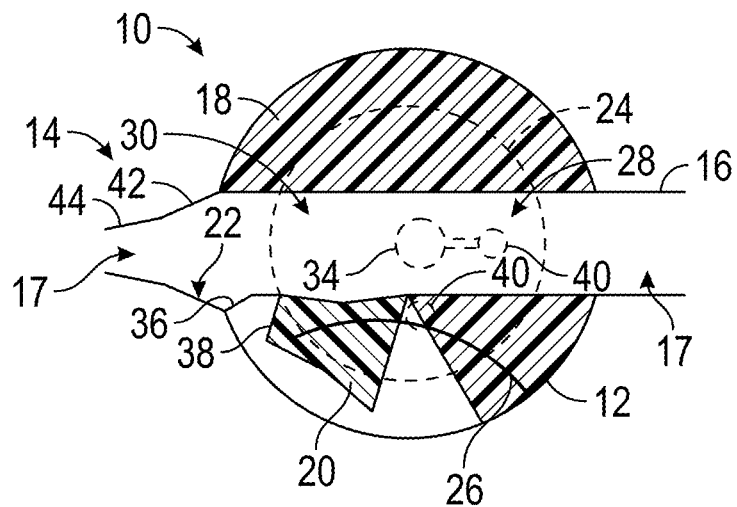
FIG. 7A shows a cross-section of an embodiment of a valve having two flow channels.
Figure 7B:
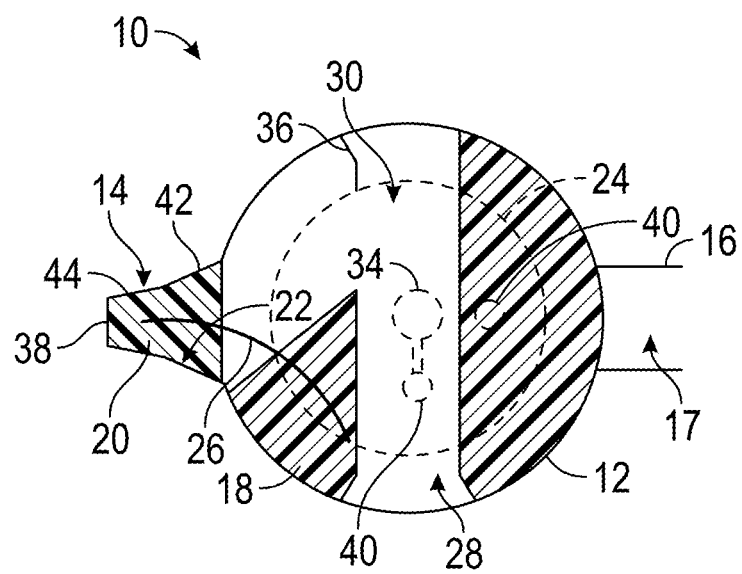
FIG. 7B shows a cross-section of the valve shown in FIG. 7A with a plug in a seat.

Although FIGS. 1, 2, and 4 show a tertiary flow channel 32 in the rotary member 18, the rotary member 18 can have any suitable number of flow channels, for example 2 to 5, specifically 2 to 3 flow channels. In an embodiment, as shown in FIGS. 7A and 7B, the rotary member 18 includes a primary flow channel 28 and secondary flow channel 30 without a tertiary flow channel 32. Such a configuration allows fluid communication between the first connector 14, the second connector 16, the primary flow channel 28, and the secondary flow channel 30 with the rotary member 18 in the first position, as in FIG. 7A. Here, the plug 20 is disposed in the plug channel (see transverse cross-sectional view in FIG. 3) of the rotary member 18. With the rotary member 18 in the second position (FIG. 7B), the plug 20 is disposed in the seat 22 such that fluid communication is impeded, e.g., stopped, from the first connector 14 but maintained from a fluid transfer device and second connector 16.

The valve 10 shown in FIG. 1 and the valve 11 shown in FIG. 7A each have two connectors, i.e., first connector 14 and second connector 16. Such a valve is a two-way valve. The valve of the implant herein can have any suitable number of connectors to allow fluid communication between any suitable number of connectors. Therefore, a valve 10a can have one connector, the valve 10 can be a two-way valve with two connectors, a three-way valve 10c with three connectors, a four-way valve with four connectors, or an n-way valve with n connectors, where n is an integer, e.g., 1 to 5. In an embodiment, the number of connectors is less than eight.

Moreover, the number of flow channels in the rotary member can be any suitable number, including 1 or greater, specifically 2 or greater, more specifically 3 or greater, even more specifically from 1 to 8, and yet more specifically from 1 to 3.

Figure 8A:
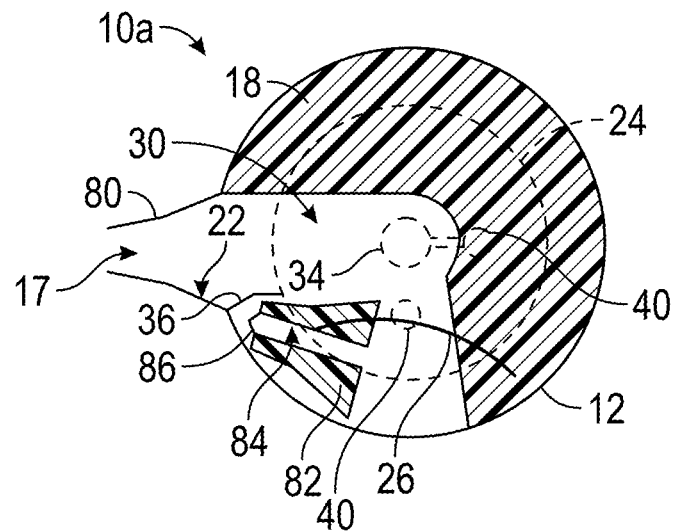
FIGS. 8A and 8B show cross-sections of an embodiment of a valve with a single connector.
Figure 8B:
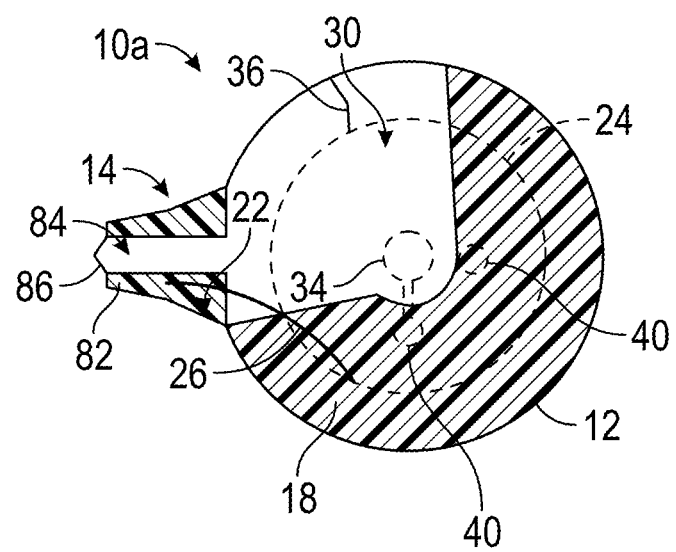

According to an embodiment, as shown in FIGS. 8A and 8B, a valve 10a can include a single connector 80. Here, a plug 82 includes a plug flow channel 84 and a plug valve 86 at an end of the plug 82. With the rotary member 18 in the position shown in FIG. 8A, the plug 82 is not seated in the seat 22, and fluid can flow through a single connector 80, fluid flow channel 17, and (when present) a fluid transfer device inserted through septum 24. As shown in FIG. 8B, with the rotary member 18 in a second position, the plug 82 is seated in the seat 22 of the first connector 14. In this configuration, fluid is blocked from flowing in a direction external to the first connector 14 toward the secondary flow channel 30 in the valve 10a. Instead, fluid can flow from a fluid transfer device (not shown) inserted through the septum 24, the secondary flow channel 30, and the plug flow channel 84 and can exit the valve 10a through plug valve 86. In this configuration, the plug valve 86 flows fluid in one direction, from the interior of the valve 10a to its exterior. Thus, when valve 10a shown in FIGS. 8A and 8B is implanted, the valve 10a can flow fluid bidirectionally per FIG. 8A or unidirectionally per FIG. 8B. The plug valve 86 can be located at any suitable location along the length of the plug 82. To avoid accumulation or growth of material, e.g., a blockage or clot near the tip of the plug 82, the plug valve 86 can be disposed at the terminus or near the terminus of the plug valve 86 as show in FIG. 8B. The plug valve 86 can be a leaf valve, for example.

Figure 8C:
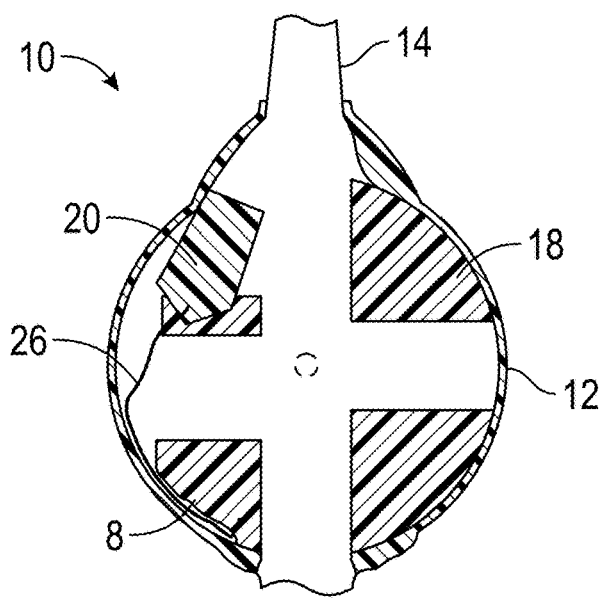
FIGS. 8C and 8D show cross-sections of another embodiment of a valve.
Figure 8D:
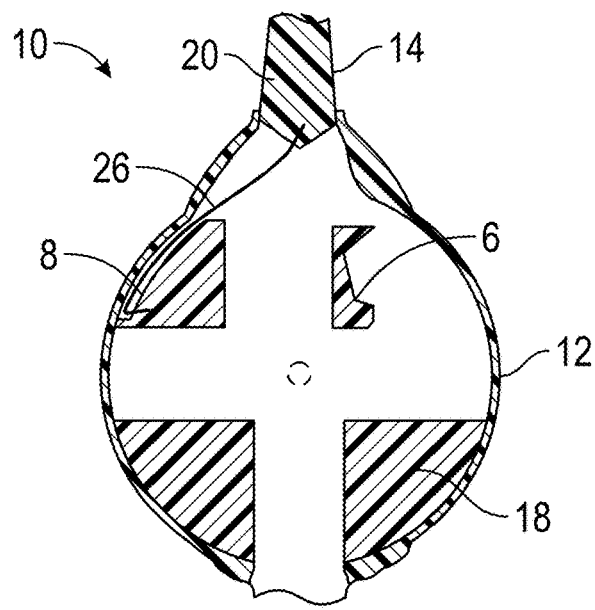

In an embodiment, the valve 10 (as shown in cross-sectional views of FIGS. 8C and 8D) can have a plug 20 connected by the coupling 26 to the rotary member 18. The coupling 26 exerts a radial force on the plug 20 such that the plug 20 is urged into the seat of the first connector 14 (FIG. 7D). Additionally, the coupling 26 supplies sufficient force on the plug 20 to allow the plug 20 to form a seal when seated in the first connector 14. In this manner, fluid will not flow through the first connector 14. It is contemplated that, although the terminus of the plug 20 may rub against an internal surface of the housing 12, the plug 20 and housing 12 will remain structurally intact and not erode due to friction or grinding caused by contact therebetween over the lifetime of the valve 10. Further, the coupling 26 can move through a groove 8 in the rotary member 18. Thus, as the rotary member 18 rotates in the housing 12, a motion or shape of the coupling 26 can be guided by a space between the groove 8 and the housing 12. In some embodiments, the rotary member 18 includes a mating surface 6 configured to receive the plug 20. That is, the mating surface 6 can have a shape complementary to a portion of the plug 20 that contacts the rotary member 18 when the plug 20 is retracted from the first connector 14 as shown in FIG. 7D.

Figure 9:
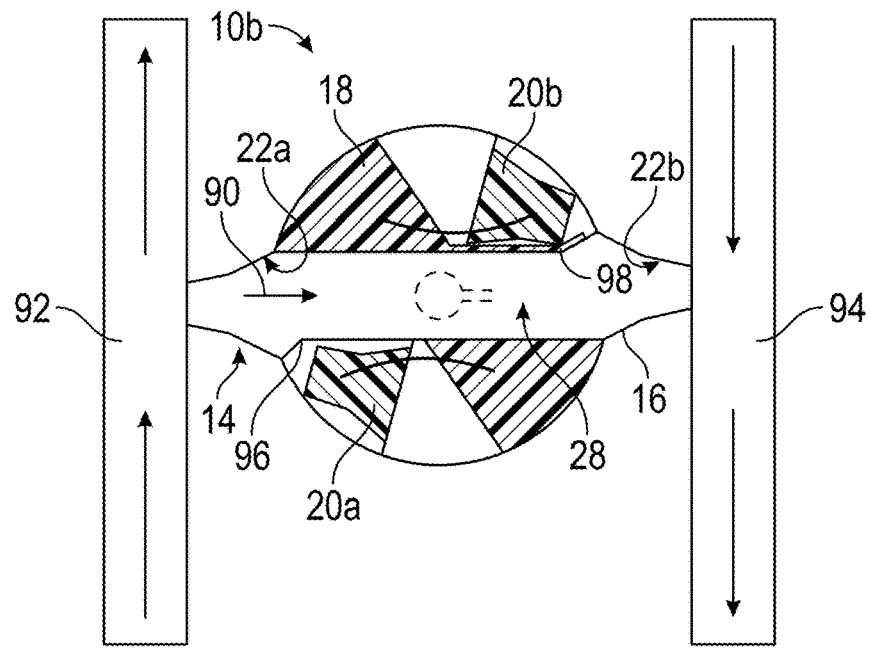
FIG. 9 shows a cross-section of an embodiment of a valve with two plugs.
Figure 10:
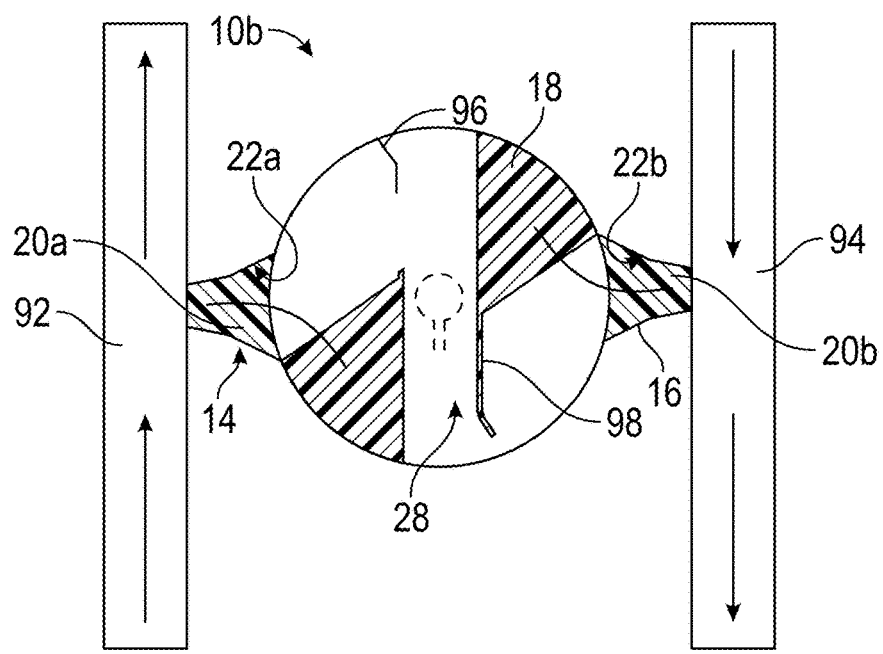
FIG. 10 shows a cross-section of the valve shown in FIG. 9 with the two plugs received in respective seats.

In an embodiment, the number of plugs 20 in the rotary member is any suitable number, including 1 or greater, specifically 2 or greater, more specifically 3 or greater, even more specifically from 1 to 8, and yet more specifically from 1 to 3. In some embodiments, the number of plugs 20 is equal to the number of connectors of the housing 12, less than the number or connectors, or greater than the number of connectors. As shown in FIGS. 9 and 10, a valve 10b can have a rotary member connected to two plugs, a first plug 20a and second plug 20b. A first seat 22a receives the first plug 20a, and a second seat 22b receives the second plug 20b. Here, the first seat 22a can be disposed proximate to or in the first connector 14, and the second seat 22b can be disposed proximate to or in the second connector 16. With this arrangement of plugs 20a, 20b and seats 22a, 22b, the rotary member 18 can be in a first position as in FIG. 9 to allow fluid communication between first connector 14 and second connector 16. However, with the rotary member 18 in the second position (FIG. 10), the first plug 20a is disposed in the first seat 22a to impede fluid communication between the first connector 14 and the primary flow channel 28, and the second plug 20b is disposed in the second seat 22b to impede fluid communication between the second connector 16 and the primary flow channel 28 such that fluid communication is impeded between the first connector 14 and second connector 16.

For the valve 10b shown in FIG. 9, a first fluid flow member 92 is connected to first connector 14, and a second fluid flow member 94 is connected to the second connector 16. A direction of fluid flow from first fluid flow member 92 and first connector 14 to the second connector 16 and second fluid flow member 94 is indicated by direction of flow arrow 90. With respect to the first position, a first baffle 96 prevents obstruction of fluid flow by the first plug 20a, and a second baffle 98 prevents obstruction of fluid flow by the second plug 20b. Here, the first baffle 96 extends from a periphery of the rotary member 18 into an interior portion of the rotary member 18 proximate to the primary flow channel 28. The second baffle 98 extends from an interior portion of the rotary member 18 toward a periphery of the rotary member 18. The length and shape of the baffle can be any suitable length and shape effective to transmit the fluid through the valve 10b without obstruction (such as to avoid turbulent flow, e.g., an eddy) produced by interference of fluid communication by the plugs 20a and 20b. In an embodiment, the seats 22a and 22b can be curved to match the profile of the plugs 20a and 20b. The first seat 22a can have a shape or size different from the second seat 22b. The number of seats 22 in the valve 10b can be equal to or less than the number of plugs 20. According to an embodiment, a tube (e.g., a biocompatible tube 520 as in FIG. 16) can be connected to the first connector 14, the second connector 16, or a combination thereof. Such a combination of the tube and the valve 10b can provide flexibility for implantation of the valve 10b, e.g., allowing the valve 10b to be located at a selectable distance or orientation relative to a vein or artery.

Figure 11:
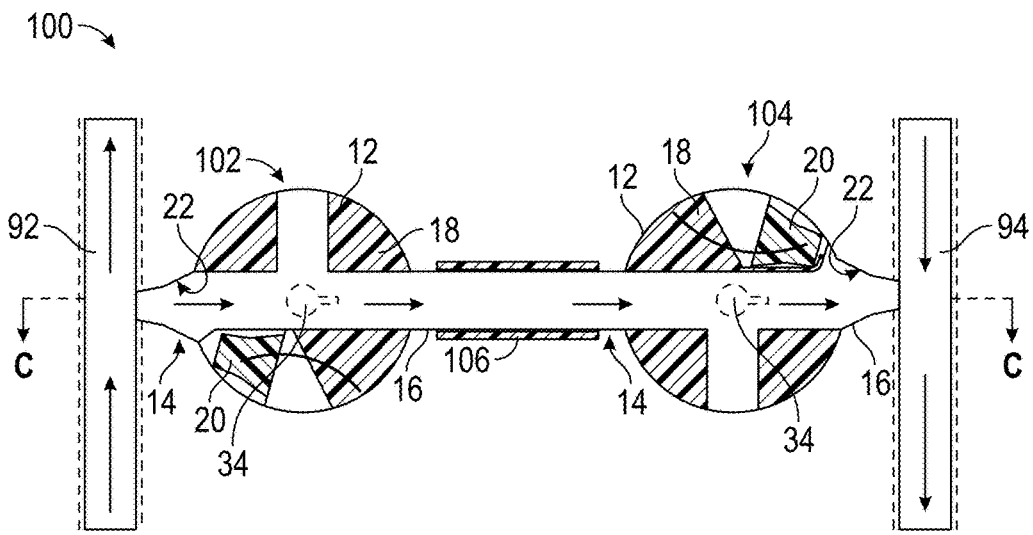
FIG. 11 shows a cross-section of an embodiment of an implant having two valves and connected to a first fluid flow member and second fluid flow member.
Figure 12:
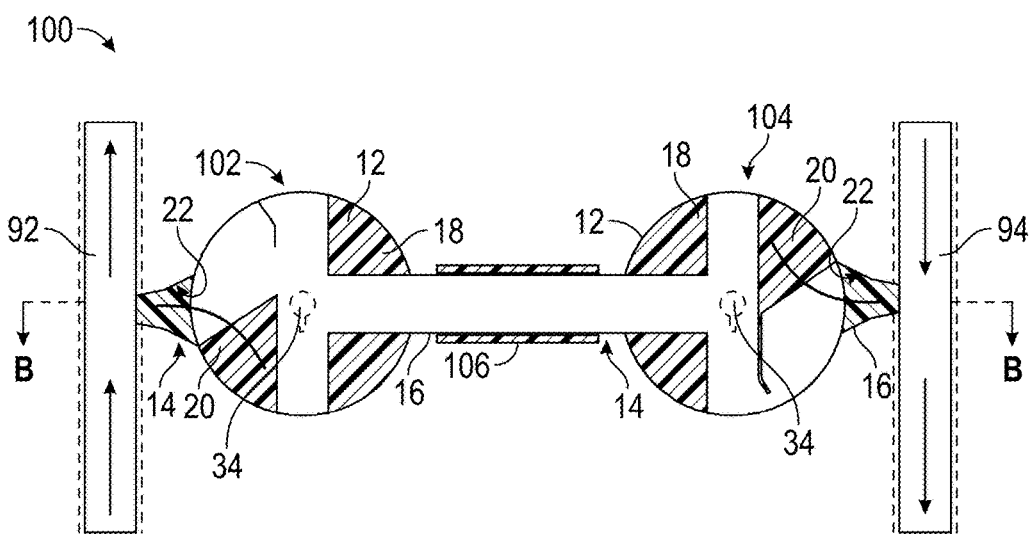
FIG. 12 shows a cross-section of the implant shown in FIG. 11 with plugs of each valve disposed in a seat.

A plurality of the valves 10, 10a, 10b in any arrangement can be present in the implant herein. As shown in FIGS. 11 and 12, the implant 100 can include a first valve 102 and a second valve 104, which are of the configuration of the valve 10. The first valve 102 can connect to the first fluid flow member 92 via first connector 14, and the second valve 104 can connect to the second fluid flow member 94 via second connector 16. The second connector 16 of the first valve 102 is connected to the first connector 14 of the second valve 104. Each valve has a housing 12, rotary member 18, keyway 34, plug 20, and seat 22, among other features in any of the previous figures of the valve. In this arrangement, fluid from the first fluid flow member 92 can flow through the first valve 102 and second valve 104 to the second fluid flow member 94. A tube, e.g., biocompatible tube 108 can connect the first valve 102 to the second valve 104.

Insertion of a fluid transfer device (not shown) into each keyway 34 of the rotary members 18 and rotation of the rotary members 18 of the first and second valves 102 and 104, respectively, rotates the rotary members 18 between their first positions shown in FIG. 11 and their second positions shown in FIG. 12. In the first position, fluid communication occurs from the first fluid flow member 92 to the second fluid flow member 94 through the first and second valves 102 and 104. In the second position, fluid communication between the first fluid flow member 92 and the second fluid flow member 94 is impeded by disposition of the plugs 20 in their respective seats 22 in the first and second valves 102 and 104. In an embodiment, the first and second valves 102 and 104 include a primary flow channel 28, a secondary flow channel 30, and a tertiary flow channel 32. The primary flow channel 28, the secondary flow channel 30, and the tertiary flow channel 32 are in fluid communication in both of the first and second positions of the rotary members 18 and plugs 20. With the rotary members 18 of the first and second valves 102 and 104 in the second position, the first and second valves 102 and 104 are in fluid communication through their respective primary flow channels 28. In this configuration, a fluid can be communicated between the first valve 102 and the second valve 104.

Figure 13:
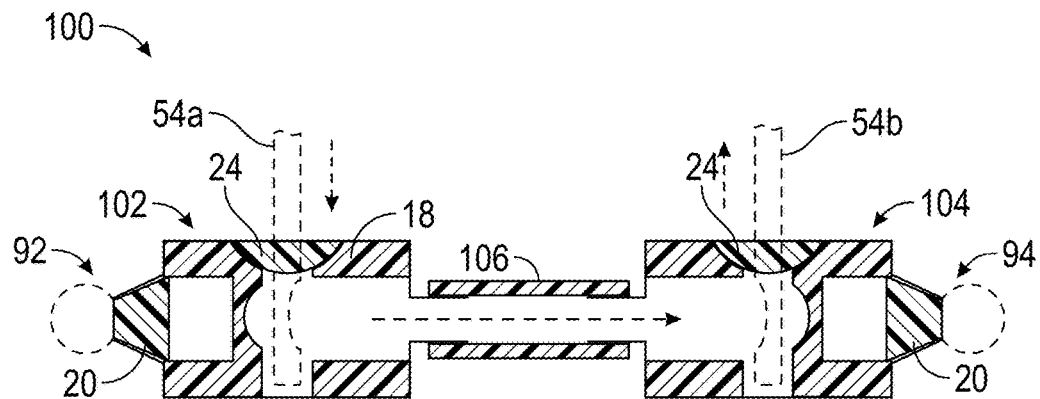
FIG. 13 shows a cross-section along line B-B of the implant of FIG. 12 connected to first and second fluid flow members with fluid communication impeded by plugs disposed in seats.

FIG. 13 is a transverse cross-section along line B-B in FIG. 12. As shown in FIG. 13, a first fluid transfer device 54a can be inserted through a septum 24 of the first valve 102, and a second fluid transfer device 54b can be inserted through a septum 24 of the second valve 104. In this manner, as indicated by the dashed arrows, a fluid can flow from a source external to the first fluid transfer device 54a, through the first valve 102, biocompatible tube 106 (if present), and second valve 104. The fluid can exit from the first and second valves 102 and 104 through second fluid transfer device 54b. Such an arrangement can flow a composition through the implant without the composition entering the first or second fluid flow members 92 and 94. The composition can dissolve, dilute, solvate, sweep, remove, or displace a fluid out of the implant introduced from the first or second fluid flow members 92 or 94, as well as remove debris or particulates from the implant if present. Here, the rotary members 18 and plugs 20 of the first and second valves 102 and 104 are in the second position as in FIGS. 2 and 12 above described.

Figure 14:
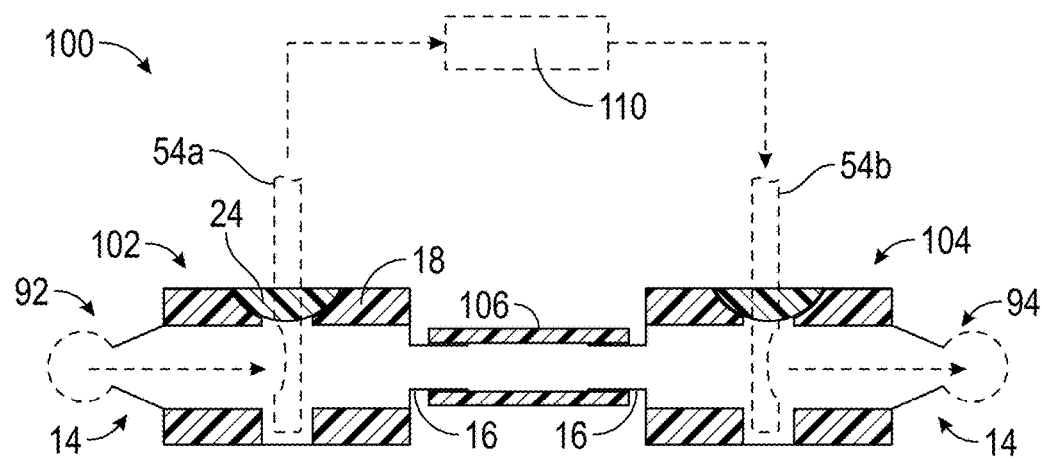
FIG. 14 shows a cross-section along line C-C of the implant of FIG. 11 connected to and in fluid communication with the first and second fluid flow members.

FIG. 14 is a transverse cross-section along line C-C in FIG. 11 with the rotary members 18 and plugs 20 (not shown) of the first and second valves 102 and 104 in the first position. With the first fluid transfer device 54a and the second fluid transfer device 54b respectively inserted through septum 24 of the first and second valves 102 and 104, fluid communication is indicated by the dashed arrows. That is, as indicated by the dashed arrows, a fluid can flow from the first fluid flow member 92, through first fluid transfer device 54a, and an external device 110 external to the implant 100, to the second fluid transfer device 54b in the second valve 104, and into the second fluid flow member 94. This arrangement communicates the fluid from the first fluid flow member 92 through the external device 110 to the second fluid flow member 94 via the first and second valves 102 and 104.

Figure 15:
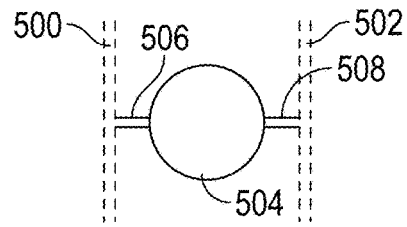
FIG. 15 is a schematic diagram which shows a configuration of an implant having a single valve connected to a first fluid flow member and second fluid flow member.
Figure 16:
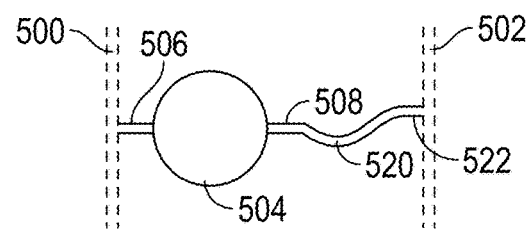
FIG. 16 is a schematic diagram which shows a configuration of an implant having a single valve and tube connected to a first fluid flow member and second fluid flow member.
Figure 17:
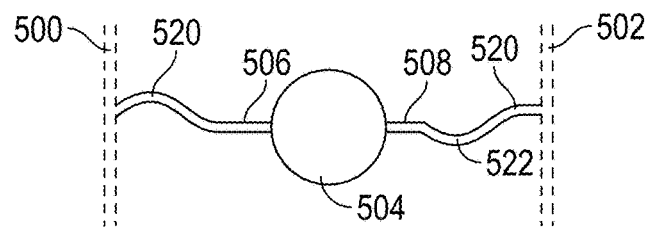
FIG. 17 is a schematic diagram which shows a configuration of an implant having a single valve interposed between tubes and connected to a first fluid flow member and second fluid flow member.

In an embodiment, the implant includes a valve 504, which is of the configuration of the valve 10, and first and second connectors 506 and 508 respectively connected to a first fluid flow member 500 and second fluid flow member 502 as shown in FIG. 15. As shown in FIG. 16, a biocompatible tube 520 can be interposed between the valve 504 and either of the first fluid flow member 500 or second fluid flow member 502. In some embodiments, a biocompatible tube 520 can be disposed between the first and second connectors 506 and 508, respectively, and the first and second fluid flow members 500 and 502, respectively, as in FIG. 17. It is contemplated that the biocompatible tube 520 can have an ancillary valve 522 disposed therein. The ancillary valve 522 can be, e.g., a leaf valve, a duckbill valve, a check valve, or a butterfly valve. The ancillary valve communicates fluid in one direction, i.e., unidirectionally, and impedes flow in the opposing direction.

Figure 18:
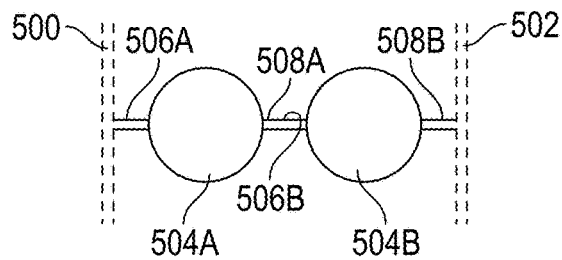
FIG. 18 is a schematic diagram which shows a configuration of an implant having two valves connected to a first fluid flow member and second fluid flow member.
Figure 19:
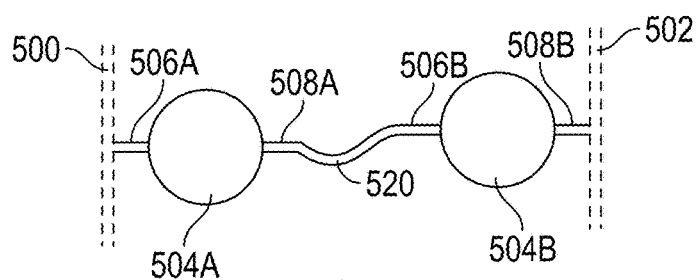
FIG. 19 shows a configuration of an implant having a tube interposed between two valves and connected to a first fluid flow member and second fluid flow member.

According to an embodiment, the implant herein includes a single valve, or a plurality of the valves, e.g., valve 10, valve 10a, or valve 10b, or a combination thereof, depending upon the number of connectors desired in each, for example, which may be connected to each other in series, parallel, or a combination thereof such that all or portion of the plurality of valves are in fluid communication. A biocompatible tube can be disposed between and interconnect at least two valves to communicate the fluid therebetween. As shown in FIG. 18, the implant can have a first valve 504A having a first connector 506A and second connector 508A, which is connected to a second valve 504B having a first connector 506B and second connector 508B. The first connector 506A and the second connector 508B can be connected to a first fluid flow member 500 and second fluid flow member 502, respectively. Again, as shown in FIG. 19, a biocompatible tube 520 can interconnect the first and second valves 504A and 504B via second connector 508A and first connector 506B.

Figure 20:
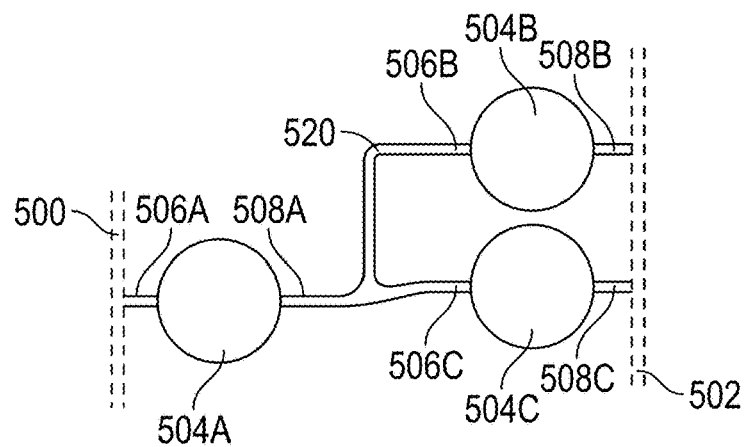
FIG. 20 is a schematic diagram which shows a configuration of an implant having a valve in series with two valves that are connected in parallel with a tube interposed between the valves, which are connected to a first fluid flow member and second fluid flow member.
Figure 21:
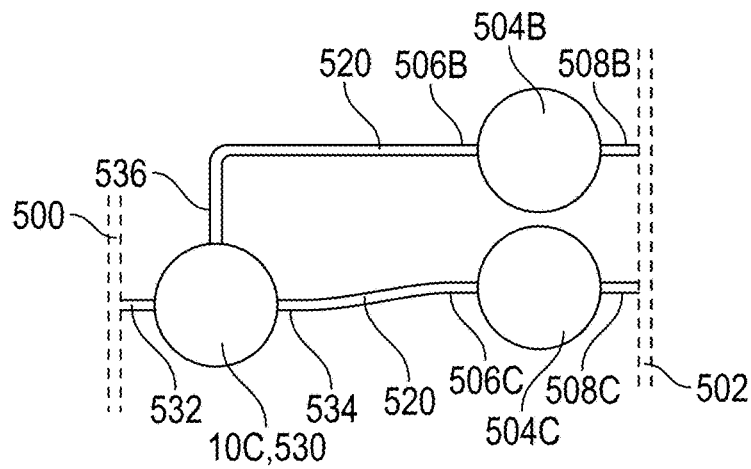
FIG. 21 is a schematic diagram which shows a configuration of an implant having a valve in series with two valves with a tube interposed between the valves, which are connected to a first fluid flow member and second fluid flow member.

As shown in FIG. 20, a first valve 504A, e.g., a two-way valve, can be connected in series to two valves, a second valve 504B and third valve 504C, which are arranged in parallel. In an embodiment, the implant herein can include a three-way valve 530 of the configuration of the valve 10c, for example, connected to another valve, e.g., second and third valves 504B and 504C, as in FIG. 21. Here, the three-way valve 530 is connected in series with the second and third valves 504B and 504C. Fluid communication between the three-way valve 530 and second and third valves 504B and 504C can be parallel or series, depending on the configuration of the fluid channels in the three-way valve 530.

As discussed above, the number of flow channels in the rotary member and connectors of the housing of the valve can be any suitable number. The flow channels can be oriented in any suitable angle to each other in the rotary member. Moreover, although connectors (e.g., the first and second connectors) have been shown as being linearly oriented on the housing, the connectors can be arranged with any angle between them.

The rotary member of the implant can have any suitable shape, including a disc, a ball, a tear, a polygonal, or a cylindrical shape. Although rotation of the rotary member has been referenced above to the first and second positions of the rotary member with respect to the housing of the valve, e.g., as shown in FIGS. 1 and 2, the rotary member can rotate from 0° to 360°, specifically 0° to 270°, more specifically 0° to 180°, even more specifically 0° to 90°, and yet more specifically 0° to 30°. The rotary member can rotate in one direction or bidirectionally with respect to the housing. In an embodiment, the housing includes a stop, and the rotary member includes a stop mate such that the stop mate engages the stop to limit the rotational range of the rotary member, e.g., between a first position and a second position. The stop can be, e.g., a protrusion extending inwardly from the housing into a race through which the rotary member is disposed and in which the rotary member rotates, and the stop mate of the rotary member can be a surface of the rotary member to engage the stop.

According to an embodiment, the housing of the valve can have any suitable external shape, including a disc, a cylindrical, a spherical, or a polygonal shape. The internal shape of the housing can be any suitable shape, including a shape complimentary to and accommodating of the rotary member.

The shape of the plug can be any suitable shape, including a cylindrical, a frustoconical, a conical, or a spherical shape. In an embodiment, as shown in FIG. 7B, the plug 20 has a terminus 38 such that when the plug 20 is disposed in the seat 22 of the valve, the terminus 38 extends to the distal end of the first connector 14. In this manner, residual fluid from, e.g., a fluid flow member (not shown) connected to the first connector 14 does not accumulate in a portion of the first connector 14 when fluid communication is impeded, by the plug 20, from the fluid flow member through the valve.

With respect to a longitudinal shape of the connector (e.g., the first, the second, and third connector) of the valve, the connector can have a single shape or multiple shapes. Non-limiting shapes include a straight, a taper, or a barbed shape. As shown in FIG. 7B, the first connector 14 has multiple shapes, including a first portion 42 having a first taper and an outer second portion 44 having a second taper, wherein the first and second tapers have different convergence angles with respect to a centerline through the first connector. A transverse cross-sectional shape of the connector can be round, polygonal, irregular, or semi-circular.

The flow channel of the rotary member of the connector (e.g., the first connector) can have any suitable cross-sectional shape to allow flow therethrough. A diameter of the flow channel can be effective to communicate fluid among the flow channels in the valve, the connectors, and the fluid flow member connected to the valve of the implant herein.

In an embodiment, the diameter of the flow channel is up to 20 millimeters (mm), specifically from 0.5 mm to 12 mm, and more specifically from 1 mm to 6 mm.

The implant components, e.g., the rotary member, plug, connector, housing, or biocompatible tube, can be made from any suitable biocompatible material. It is contemplated that these materials are biostable, having a long lifetime before and after implantation in a patient, e.g., 15 years or greater, and specifically 10 years or greater. Although some portion of the implant can be biologically absorbable, the implant and its components will remain intact and function as above.

In an embodiment, the biocompatible materials include a metal, polymer, ceramic, and the like. Such materials can include those that have been approved by the United States Food and Drug Administration (USFDA). Exemplary metals include tungsten, stainless steel, titanium, vanadium, aluminum, cobalt chromium, nickel, molybdenum, gold, zirconium, tantalum, niobium, hafnium, rhenium, alloys thereof, or a combination thereof. Exemplary alloys include titanium-vanadium-aluminum, nickel-titanium (nitinol), cobalt-chromium, cobalt-chromium-molybdenum, or cobalt-nickel-chromium-molybdenum.

Exemplary polymers include acrylate, methacrylate polymers (such as poly(methyl methacrylate)), polyetheretherketone (PEEK), polycarbonates, polyethylene (PE) (including high density polyethylene (HDPE), medium density polyethylene, low density polyethylene (LDPE), cross-linked high density polyethylene (XLPE), linear low density polyethylene (LLDPE), ultra-low density polyethylene, and very low density polyethylene), oxidized polyethylene, polypropylene (PP), polypropylene copolymer (PPCO), polyisobutylene, polystyrenes, polysulfones, polyethersulfones, polyarylsulfones, polyarylethers, polyolefins, polyacrylates, polyvinyl derivatives, cellulose derivatives, polyurethanes, polyamides, polyimides, polyesters, silicone resins, epoxy resins, polyvinyl alcohol, polyacrylic acid, polyallomer (PA), polymethylpentene (PMP or TPX), polyketone (PK), polyethylene terephthalates (PET) (including polyethylene terephthalate G copolymer (PETG) and oriented PET), polystyrene (PS), polyvinylchloride (PVC), naphthalate, polybutylene terephthalate, mixtures thereof, copolymers thereof, or a combination thereof.

In an embodiment, the polymer is a fluoropolymer. Exemplary fluoropolymers include ethylene-chlorotrifluoroethylene copolymer (ECTFE) (commercially available under the trade name Halar from Allied Chemical Corporation), ethylene-tetrafluoroethylene (ETFE) (commercially available under the trade name Tefzel from EJ. DuPont de Nemours and Co. Wilmington, Del.), tetrafluoroethylene (TFE), polytetrafluoroethylene fluorinated ethylene propylene (PTFE-FEP), polytetrafluoroethylene (PTFE), polyethylenefluoride, polytetrafluoroethylene perfluoroalkoxy (PTFE-PFA), polyvinylidene fluoride (PVDF), or a combination thereof.

Exemplary ceramics include silica, alumina, zirconia, and titania.

In an embodiment, the components of the implant include a different or same material. The rotary member and housing of the valve can be made from materials that are strong and that allow rotation of the rotary member in the housing with little friction or wear of the rotary member or housing. For example, the rotary member or housing can include a material with favorable tribological characteristics such as PTFE. The septum can include a material (e.g., silicone rubber, PTFE, polyethylene, polypropylene, copolymers of hexafluoropropylene (HFP) and vinylidene fluoride (VDF or VF2), terpolymers of tetrafluoroethylene (TFE), vinylidene fluoride (VDF) and hexafluoropropylene (HFP), or perfluoromethylvinylether (PMVE)) that is resilient to deterioration of repeated insertions or rotation of the fluid transfer device while maintaining its ability to seal around the fluid transfer device and reseal once the fluid transfer device is removed from the septum.

The coupling, which connects the plug to the rotary connector, as in FIG. 1, can be rigid or flexible and can include a springy material such as stainless steel, tungsten, a polyetherimide (available under the trade name Ultem commercially available from SABIC Innovative Plastics), or polyetheretherketone (PEEK), or a combination thereof.

According to an embodiment, with reference to, e.g., FIG. 1, the first portion 42 of a connector, e.g., the first connector 14 (distal from the rotary member 18) includes a metal (e.g., stainless steel), and the second portion 44 of the first connector 14 includes a polymer (e.g., an acrylic or PTFE). In this arrangement, the first connector 14 has sufficient mechanical strength to connect to a fluid flow member for an extended period of time. It should be appreciated that any of the connectors of the valve herein can be similarly structured as the first connector.

In an embodiment, the fluid transfer device can be a device such as a syringe, hollow bore needle, cannula, catheter, and the like to transfer a fluid from the implant to an external fluid communication device or system, e.g., a dialysis device. Further, the fluid transfer device can be any shape to provide engagement with the rotary member 18 and particularly the keyway 34. A cross-sectional shape of the fluid transfer device (e.g., fluid transfer device 54 shown in FIG. 5) can include a symmetrical or an asymmetrical shape.

According to an embodiment, a biocompatible agent can be included in the material or attached to a surface of the implant to improve biocompatibility thereof. The biocompatible agent may be a growth factor such as endothelial cell growth factor, epithelial cell growth factor, osteoblast growth factor, fibroblast growth factor, platelet derived growth factor, neural growth factor, or angiogenin growth factor; an antimicrobial agent such as lysosyme or penicillin; an antithrombogenic agent such as heparin, albumin, streptokinase, tissue plasminogen activator (TPA) or urokinase; a thrombogenic agent such as collagen or a hydrophilic polymer such as polyethylene glycol, hyaluronic acid, chitosan or methyl cellulose, or other proteins, carbohydrates, fatty acids, or the like, or a combination thereof.

The implant herein can be made in various ways. In an embodiment, a method for making the implant includes forming a rotary member, forming a plurality of flow channels in the rotary member such that the flow channels are in fluid communication; connecting a plug to the rotary member, forming a housing, disposing the rotary member and plug in the housing, and disposing a septum on the housing with the septum being in sealing contact with housing to receive a fluid transfer device. In addition, the method can include forming a seat in the housing such that the seat is arranged proximate to or disposed in the first connector to sealingly receive the plug.

Forming the rotary member, housing (including connectors), plug, septum, or other component of the implant can include molding (e.g., blow molding, compression molding, and the like), extrusion, casting, printing (e.g., three-dimensional printing), and the like. In an embodiment, the housing can be formed around the rotary member or can be made such that the rotary member is disposed in part of the housing and the remaining portion of the housing combined with the portion having the rotary member. Thus, the housing can be formed in a single piece or as a plurality of pieces that are combined together in the implant. The connectors of the housing can be integrally formed with the housing or attached thereto in a physical or chemical manner such as press fitting, screwing, bonding, adhering, and the like. Disposal of the septum on the housing can be achieved, e.g., by bonding and the like.

Connecting the plug to the rotary member can include interposing the coupling between the rotary member and plug. The first end of the coupling can be disposed in the rotary member or bonded (e.g., using a curable adhesive) or physically attached to a surface of the rotary member (e.g., using fastener such as a staple). The second end of the coupling is attached to the plug in a manner that can be the same or different as attachment of the first end of the coupling to the rotary member.

The keyway and flow channels in the rotary member can be formed as the rotary member is formed, e.g., by molding. Alternatively, the keyway and flow channels can be formed by removing material from the rotary such as by milling, drilling, cutting, etching, and the like.

The baffle of the rotary member can be integrally formed as part of the rotary member during formation of the rotary member or as a consequence of removing material from the rotary member to form the flow channels or keyway. Additionally, the baffle can be formed by addition of material to the rotary member. The baffle can then be attached to the interior of the rotary member via chemical or physical attachment.

The method of making the implant can also include connecting a plurality of valves. Connection of the plurality of valves can include disposing a biocompatible tube between at least two valves to communicate a fluid between the at least two valves. Alternatively, the valves can be connected together chemically (e.g., using an adhesive) or physically (e.g., press fitting connectors of the valves together). In an embodiment, the plurality of valves can be formed together, e.g., by molding, such that the connectors of valves that are in fluid communication through their connectors are a single piece or fused together. For the plurality of valves, connections among the connectors of the valves desirably do not leak the fluid.

The implant herein has advantageous characteristics including control of fluid communication through the valve, biocompatibility, short maturation time once implanted, long lifetime, controllable flow rate, scalable size, rigidity or flexibility depending on the application due to the materials that can be used in the construction of the valve, light weight construction, adaptability to any combination of series or parallel flow configurations, robust design, ease of use, and the like. In addition, since the plug can be disposed in the seat of the connector (e.g., first connector) of the valve of the implant such that the plug extends to the terminus of the connector distal to the housing, the connector of the implant beneficially does not have a void volume in which residual fluid can be disposed. Thus, the implant advantageously does not retain fluid material, e.g., blood, which can accumulate, stagnate, or impede fluid communication through the valve. Further as the plug is disposed in the seat of the connector, the plug urges fluid out of the connector to an exterior of the implant. In this manner, the plug can remove fluid from the connector, particularly the seat of the connector. In an embodiment, a volume of at least an outer portion of the connector is filled by the plug.

The implant herein can be used for a plurality of purposes, uses, environments, or subjects. Further, the implant can be combined with other implantable devices. In an embodiment, the implant is a catheter, port (e.g., vascular or dialysis), infusion device, dialysis implant, drug delivery system, or drain. According to an embodiment, the implant is a dialysis shunt. In an embodiment, the implant is a hemodialysis graft or a fistula.

Figure 22:
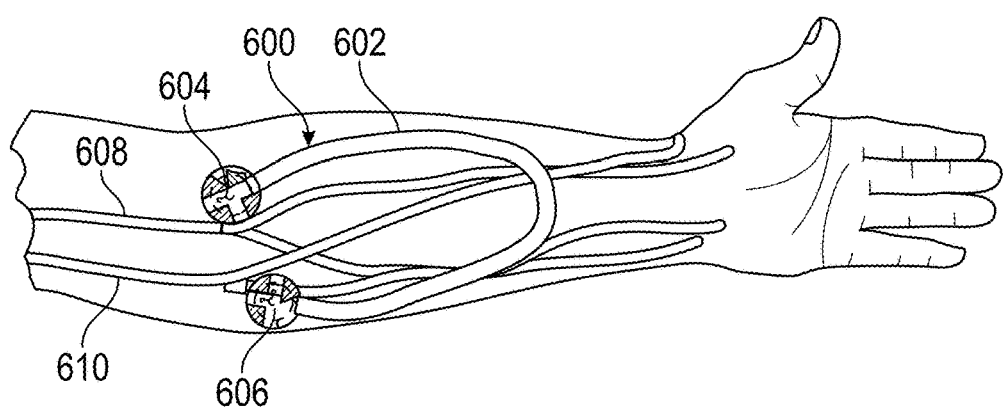
FIG. 22 shows an embodiment of an implant disposed in a human arm.

According to an embodiment, as shown in FIG. 22, the implant 600 is the graft, and the implant 600 includes a biocompatible tube 602 interposed between a first valve 604 and a second valve 606, both of which may comprise the configuration of the valve 10a, for example, which are respectively connected to first fluid flow member 608 and second fluid flow member 610. The implant 600 can be disposed in any suitable location, such as in an arm 612 of a patient. Disposing the implant in a leg or in the chest is also specifically mentioned. The first and second fluid flow members 608 and 610 can be a blood vessel. In an embodiment, the first valve 604 connects to an artery 608, and the second valve 606 connects to a vein 610 such that the biocompatible tube 602 communicates fluid between the first valve 604, second valve 606, artery 608, vein 610, or a combination thereof. The fluid can be, e.g., blood, saline, a medicament, or a combination thereof.

Thus, the implant herein can be used in many ways. In an embodiment, a method may comprise disposing (e.g., implanting) the implant into a patient. In an embodiment, a method for performing dialysis may comprise, locating the implant disposed in the patient, inserting the fluid transfer device through the septum of the implant, inserting the fluid transfer device in the keyway of the valve, rotating the fluid transfer device with respect to the housing of the valve, rotating the rotary member in response to rotating the fluid transfer device, and communicating a fluid in the implant to perform dialysis.

Disposing the implant can include connecting the first connector of the implant to an artery of the patient and connecting the second connector to a vein of the patient. The implant can be affixed to the vein or artery using a suture or a clip. Once implanted, the implant can be located, and the orientation of the implant can be determined by locating the position indicator on the surface of the septum, e.g., by palpation of the skin proximate to the valve of the implant. The rotational orientation of the rotary member in the housing can then be determined, e.g., by comparing the position indicator (which can correlate with the position of the connectors of the housing) with a protrusion of the fluid transfer device. In an embodiment, a position indicator is absent from the septum, and a position of the rotary member with respect to the housing can be determined by the orientation of the fluid transfer device with respect to a connector on the housing.

When the plug is not disposed in the seat, i.e., the rotary member is in the first position, blood can communicate from the artery through the first connector, the secondary flow channel of the valve, and the fluid transfer device. Further, the method can include communicating the blood from the artery to a dialysis device (e.g., a dialysis machine) and dialyzing the blood from the artery with the dialysis device to form dialyzed blood. The dialyzed blood can be communicated from the dialysis device, through the fluid transfer device, the primary flow channel, and the second connector, and to the vein of the patient.

Fluid communication from the vein or the artery through the implant can be stopped by rotating the fluid transfer device with respect to the housing to effect rotation of the rotary member from the first position to the second position in response to rotating the fluid transfer device. Thus, the plug may be disposed in the seat to impede flow from the artery or to the vein. Consequently, removal or return of blood from a vein or artery during dialysis can be terminated in this manner or momentarily interrupted and reinitiated by returning the rotary member to the first position to allow fluid communication again.

After isolating the implant from the vein and artery, residual blood, biological fluid, or other fluid can remain disposed in the implant. Without wishing to be bound by theory, it is believed that such material can clot, agglomerate, or otherwise accumulate after single or repeated use of the implant. Various fluids, e.g., blood, can form a material (e.g., a clot) that can be particulate or that can coat an internal surface of the implant, which can impede fluid communication through the valve and decrease the lifetime and efficiency of the implant. To remove residual fluid from the implant, the method includes communicating, e.g., administering, a postdialysis composition in the fluid transfer device and disposing the postdialysis composition in the implant from the fluid transfer device. The composition can comprise an anticoagulant (e.g., heparin), saline, water, an antibacterial agent, or a combination thereof. Heparinized saline is specifically mentioned. In an embodiment, the residual fluid, e.g., blood, is removed and replaced with the postdialysis composition, e.g., heparinized saline. Further, the postdialysis composition can be purged from the implant and replaced by another composition that remains in the implant between dialysis treatments. The fluid transfer device can then be removed from the implant.

In an embodiment, the implant can include a plurality of valves (e.g., a first and second valve) such that the method can include communicating a postdialysis composition in the first fluid transfer device, disposing the postdialysis composition in the first valve from the first fluid transfer device, communicating the postdialysis composition from the first valve to the second valve, communicating the postdialysis composition from the second valve to the second fluid transfer device, and removing a thrombolytic material, debris, contaminant, blood, or a combination thereof, if present, from the implant.

Figure 23A:
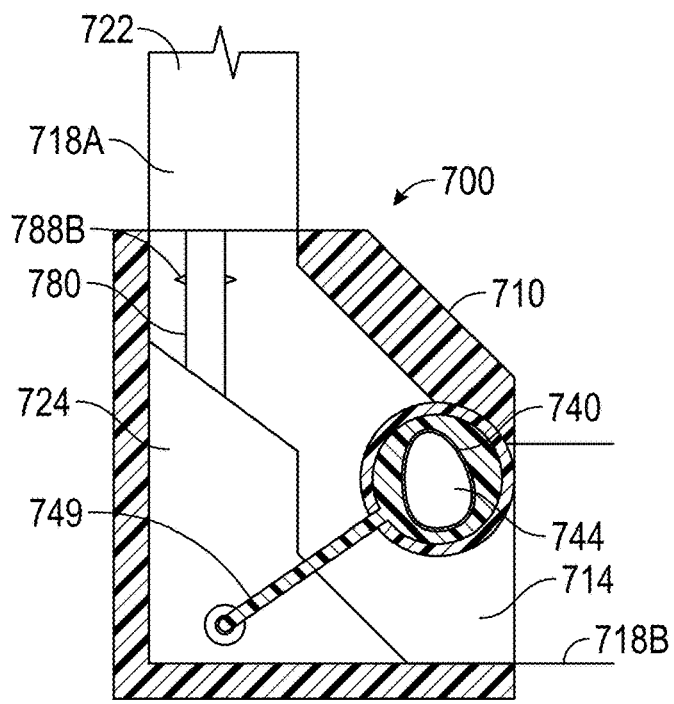
FIGS. 23A and 23B each depict a cross-section of an embodiment of an valve.
Figure 23B:
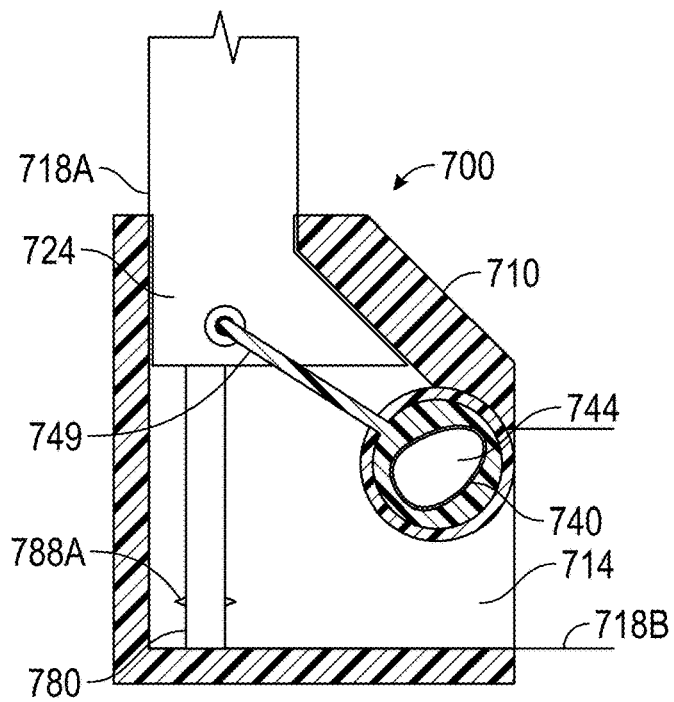
Figure 24:
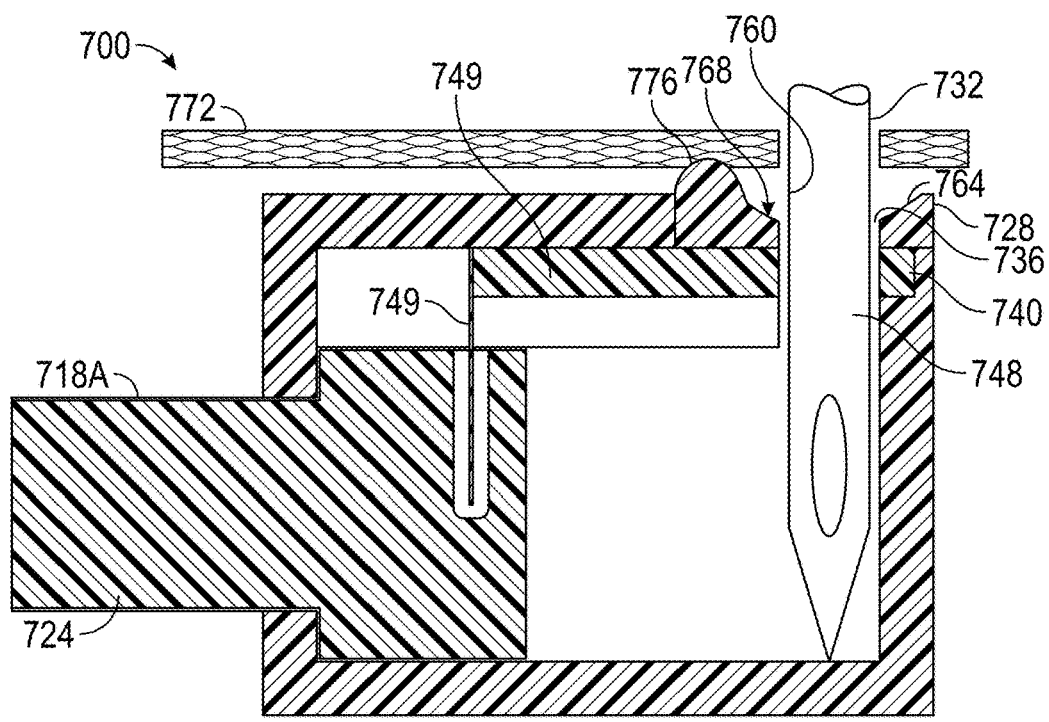
FIG. 24 depicts a cross section of an embodiment of an valve disclosed herein.

Referring to the cross sectional views of FIGS. 23A, 23B, and 24, another embodiment of the valve 700 is shown. The valve 700 includes a housing 710 defining a cavity 714 having at least one connector, for example a first connector 718A and a second connector 718B, each providing fluidic communication between the cavity 714 and an outside 722 of the housing 710. The valve 700 shares the configuration of the valve 10 at least concerning the number of connectors employed. The valve 700 also includes a plug 724 movable, e.g., slidably movable, within the housing 710 between at least a first position shown in FIG. 23B and a second position shown in FIG. 23A. In the first position the plug 724 occludes fluidic communication between the cavity 714 and the outside 722 while in the second position allows fluidic communication between the cavity 714 and the outside 722 through the connector 718A. The plug 724 may slidably engage the first connector 718A. A septum 728 (shown in cross-section in FIGS. 24 and 25) is sealingly engaged to the housing 710 thereby preventing fluidic communication from the cavity 714 to the outside 722. The septum 728 is sealingly penetrable by a fluid transfer device 732 that is capable of moving the plug 724 between at least the first position and the second position, while transferring fluid therethrough all the while. The septum 728 is able to seal itself to fluidic transfer through an opening 736 therein that the fluid transfer device 732 has penetrated through after removal of the fluid transfer device 732. The fluid transfer device 732 may be a syringe, a hollow bore needle, a cannula, or a catheter, for example. The valve 700 is further configured to be engaged and disengaged repeatedly with the fluid transfer device 732 of a similar fluid transfer device.

The valve 700 may have any suitable number of connectors. In an embodiment, the valve 700 may include a single connector, or 2 to 4 connectors. Shown in FIG. 23A is an embodiment having first and second connectors 718A and 718B. Use of multiple connectors allows the valve 700 when implanted to be connected to more than one blood vessel or biocompatible tube (not shown in these Figures). In such an embodiment, the first and second connectors 718A and 718B can serve as a shunt and allow fluidic communication between different fluid flow members as illustrated in FIGS. 9 and 10, for example. Such fluid flow members can also include a vein and an artery. When the plug 724 is in the first position fluidic communication therebetween is occluded and when the plug 724 is in the second position, such fluidic communication is allowed.

Figure 25:
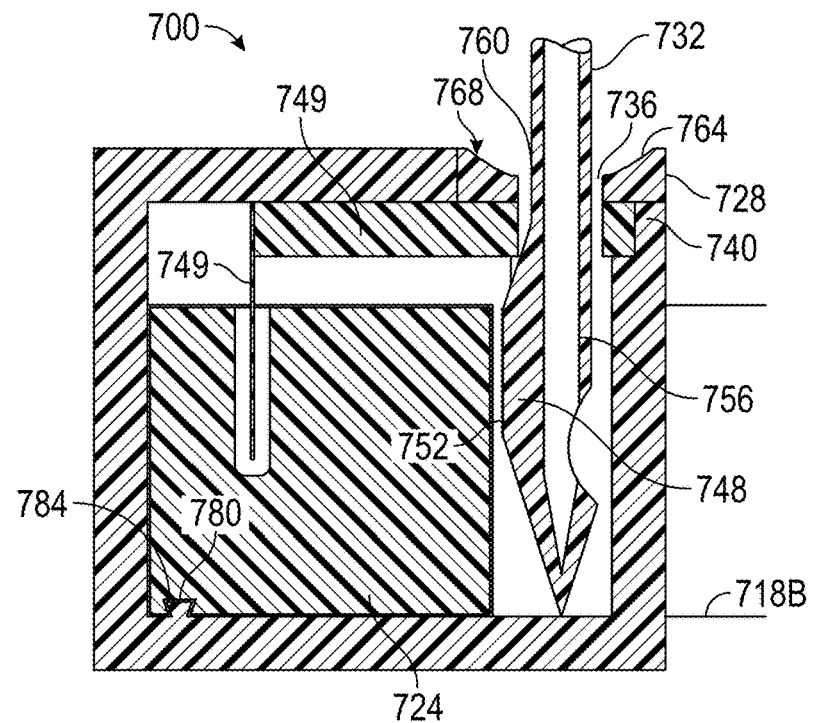
FIG. 25 depicts a cross section of an embodiment of a valve disclosed herein.

Referring to FIGS. 24 and 25, the valve 700 includes a rotor 740 positioned within the cavity 714 proximate the septum 728 that has a keyway 744 receptive to the fluid transfer device 732. At least a portion of the keyway 744 in the rotor 740 is noncircular and is complementary to a shape of a keyed portion 748 of the fluid transfer device 732. As such, the fluid transfer device 732 can act as a key and cause the rotor 740 to rotate upon rotation of the fluid transfer device 732. A coupling 749 in operable communication with both the rotor 740 and the plug 724 causes the plug 724 to move between the first position and the second position in response to rotation of the rotor 740.

A rail 780, best seen in FIGS. 23A and 23B, guides the plug 724 when moved between the first and second positions. A groove 784 (see FIG. 25) in the plug 724 is slidably engaged with the rail 780. Frictional engagement between the groove 784 and the rail 780 can maintain the plug 724 in any position when not being actively moved by the fluid transfer device 732. Alternately or in addition, other features can be incorporated in the rail 780 and groove 784 to both prevent undesirable movement of the plug 724 as well as provide feedback to the operator, e.g., tactile feedback, when the plug 724 has been fully moved to the first position, the second position or any other desired position. Such features could include protrusions 788A, 788B on the rail 780 that engage with an undercut (not shown) in the plug 724 to provide a "click" when the plug 724 is fully seated at the first position and the second position respectively. Other sets of components that experience relative movement when the plug 724 is moved could also or alternately employ features to provide feedback of position of the plug 724 including, the septum 728 and the housing 710, and the coupling 749 and the housing 710, for example.

The plug 724 may be sized and shaped to substantially fill a volume defined by the first connector 718A, specifically an outer portion of the first connector distal to the cavity, when the plug is in the first position occluding the connector 718A. This filling of the volume eliminates a void in which a fluid such as blood could pool and potentially form a clot or other accumulation.

The noncircular shape of the keyway 744 and the keyed portion 748 of the fluid transfer device 732 can, for example, be oval (as shown in FIGS. 23A, 23B and 24), or have a blade 752 protruding from a tubular portion 756 (as shown in FIG. 25). Regardless of the shape of the keyway 744 and the keyed portion 748 of the fluid transfer device 732, the opening 736 in the septum 728 may be circular. Having the opening 736 be circular can facilitate sealingly engaging a circular portion 760 of the fluid transfer device 732 that is positioned proximate the septum 728 when fully engaged within the valve 700 and rotating as well as to self-seal the septum 728 upon removal of the fluid transfer device 732 from the septum 728. Having the keyed portion 748 and the circular portion 760 displaced from one another longitudinally along the fluid transfer device 732 requires a transition between the two differently shaped cross sectional portions in an area anticipated to be between the rotor 740 and the septum 728 when the fluid transfer device 732 is fully inserted in the valve 700.

Additionally, the septum 728 can have a depression 764 in a surface 768 thereof. The presence of the depression 764 can serve a few purposes. The depression 764 aids in locating the opening 736 in the septum 728 thereby facilitating insertion of the fluidic transfer device 732 into the proper location on the valve 700 during each attempt. The depression 764 also allows a patient's skin 772 (shown in FIG. 24 only) positioned proximate the septum 728 to be pierced by the fluidic transfer device 732 without the skin 772 being pinched against the surface 768 that could damage the skin 772.

The septum 728 can also include a position indicator 776 (shown in FIG. 25 only) that protrudes from the surface 768. The position indicator 776 can be correlated to the position of the plug 724 within the housing 710. The position indicator also provides information as to what direction the keyway 744 is oriented so that the fluidic transfer device 732 can be inserted in the correct orientation relative to the keyway 744.

An implant may comprise the valve 700 and first and second connectors 718A and 718B. In an embodiment, the implant any suitable number of the valves 700, e.g., 1 to 4 valves, specifically 1 to 2 valves, with varying numbers of the connectors 718A, 718B in a fashion similar to that discussed with reference to FIGS. 1-14 and 16-22.

In an embodiment, an implant comprises a valve comprising: a housing comprising a first connector protruding from the housing to connect to a first fluid flow member and to communicate a fluid, and a second connector protruding from the housing to connect to a second fluid flow member and to communicate the fluid, a rotary member disposed in the housing, a plug disposed in the housing and connected to the rotary member, a seat arranged proximate to or disposed in the first connector to sealingly receive the plug, and a septum disposed on and in sealing contact with the housing to receive a fluid transfer device.

In various embodiments (i) the implant further comprises a coupling to connect the plug to the rotary member; and/or (ii) the coupling is flexible and is configured to exert an outwardly radial force on the plug to urge the plug into the seat in response to the plug being proximate to the seat; and/or (iii) the rotary member comprises a primary flow channel and a secondary flow channel disposed in the rotary member, the primary flow channel being in fluid communication with the secondary flow channel; and/or (iv) the rotary member is configured to rotate between a first position and a second position; and/or (v) with the rotary member in the first position, the first connector, the second connector, the primary flow channel, and the secondary flow channel are in fluid communication; and/or (vi) with the rotary member in the second position, the plug is disposed in the seat to impede fluid communication between the first connector and the second connector; and/or (vii) the rotary member further comprises a tertiary flow channel in fluid communication with the primary flow channel and the secondary flow channel; and/or (viii) with the rotary member in the second position, the second connector, the primary flow channel, the secondary flow channel, and the tertiary flow channel are in fluid communication; and/or (ix) with the rotary member in the second position, the rotary member is arranged to impede fluid communication between the first connector and the primary and the secondary flow channels; and/or (x) two plugs and two seats are present in the valve: a first seat to receive a first plug, and a second seat to receive a second plug, wherein the first seat is disposed proximate to or in the first connector, and the second seat is disposed proximate to or in the second connector; and/or (xi) with the rotary member in the second position, the first plug is disposed in the first seat to impede fluid communication between the first connector and the primary flow channel, and the second plug is disposed in the second seat to impede fluid communication between the second connector and the primary flow channel; and/or (xii) the rotary member further comprises a plug channel, and the plug is configured to move in response to rotation of the rotary member such that the plug traverses the plug channel in response to rotation of the rotary member between the first position and the second position; and/or (xiii) the coupling comprises: a first end attached to the rotary member, a second end attached to the plug, and an intermediate portion interposed between the first end and the second end, the intermediate portion being disposed in the plug channel; and/or (xiv) the rotary member comprises a keyway to receive the fluid transfer device; and/or (xv) the rotary member is configured to rotate in response to insertion and rotation of the fluid transfer device in the keyway; and/or (xvi) the rotary member further comprises a baffle to obstruct contact between the plug and a flow of the fluid between the first connector and the second connector; and/or (xvii) the baffle extends from a periphery of the rotary member into an interior portion of the rotary member; and/or (xviii) the baffle extends from an interior portion of the rotary member toward a periphery of the rotary member; and/or (xix) the septum comprises a position indicator disposed on a surface opposing the rotary member, the position indicator protruding from the surface of the septum; and/or (xx) the septum is configured to seal around the fluid transfer device in response to insertion of the fluid transfer device through the septum, and the septum is configured to impede fluid communication between an interior and exterior of the valve; and/or (xxi) the first fluid flow member comprises a blood vessel or a biocompatible tube, and the second fluid flow member comprises a blood vessel or a biocompatible tube; and/or (xxii) the first fluid flow member is an artery, and the second fluid flow member is a vein; and/or (xxii) further comprising a biocompatible tube interposed between the first connector and the artery, the second connector and the vein, or a combination thereof; and/or (xxiii) a plurality of valves are present in the implant; and/or (xxiv) the plurality of valves are connected to each other in series, parallel, or a combination thereof, such that all or portion of the plurality of valves are in fluid communication; and/or (xxv) a biocompatible tube is disposed between and interconnects at least two valves to communicate the fluid between the at least two valves; and/or (xxvi) the first connector comprises a straight portion, a taper portion, or a combination thereof, a terminus of the first connector, which is distal from the rotary member, comprises a metal, a polymer, a ceramic, or a combination thereof to connect the first connector to the first fluid flow member, the second connector comprises a straight portion, a taper portion, or a combination thereof, and a terminus of the second connector, which is distal from the rotary member, comprises a metal, a polymer, a ceramic, or a combination thereof to connect the second connector to the first fluid flow member; and/or (xxvii) the housing comprises a metal, a polymer, a ceramic, or combination thereof; and/or (xxviii) the rotary member comprises a metal, a polymer, a ceramic, or combination thereof; and/or (xxix) the plug comprises a metal, a polymer, a ceramic, or combination thereof; and/or (xxx) the septum comprises a polymer; and/or (xxxi) the coupling comprises a metal, a polymer, or combination thereof; and/or (xxxii) the implant is a hemodialysis graft or a fistula; and/or (xxxiii) the implant is the graft, and the implant further comprises a biocompatible tube interposed between a first valve of claim 1 and a second valve of claim 1, the biocompatible tube configured to communicate the fluid between the first valve, the second valve, a vein, an artery, or a combination thereof; and/or (xxxiv) the biocompatible tube is flexible and comprises a stable biocompatible material; and/or (xxxv) a portion of the valve is configured to communicate the fluid which comprises blood, saline, a medicament, or a combination thereof.

In another embodiment a method for making an implant, comprises: forming a rotary member, forming a plurality of flow channels in the rotary member, the flow channels being in fluid communication, connecting a plug to the rotary member, forming a housing, disposing the rotary member and the plug in the housing, and disposing a septum on the housing, the septum being in sealing contact with the housing to receive a fluid transfer device.

In other various embodiments, (i) the housing comprises: a first connector protruding from the housing to connect to a first fluid flow member, and a second connector protruding from the housing to connect to a second fluid flow member; and/or (ii) further comprising forming a seat in the housing arranged proximate to or disposed in the first connector to sealingly receive the plug; and/or (iii) connecting the plug to the rotary member comprises interposing a coupling between the rotary member and the plug, such that a first end of the coupling is attached to the rotary member, a second end of the coupling is attached to the plug, and an intermediate portion of the coupling is interposed between the first end and the second end, the intermediate portion being disposed in a plug channel of the rotary member; and/or (iv) the coupling is flexible and is configured to exert an outwardly radial force on the plug to urge the plug into the seat in response to the plug being proximate to the seat; and/or (v) the plurality of flow channels in the rotary member comprises a primary flow channel and a secondary flow channel; and/or (vi) the rotary member is configured to rotate between a first position and a second position; and/or (vii) the rotary member in the first position, the first connector, the second connector, the primary flow channel, and the secondary flow channel are in fluid communication; and/or (viii) the rotary member in the second position, the plug is disposed in the seat to impede fluid communication between the first connector and the second connector; and/or (ix) the rotary member further comprises a tertiary flow channel in fluid communication with the primary flow channel and the secondary flow channel; and/or (x) the rotary member in the second position, the second connector, the primary flow channel, the secondary flow channel, and the tertiary flow channel are in fluid communication; and/or (xi) the rotary member in the second position, the rotary member is arranged to impede fluid communication between the second connector and the primary and the secondary flow channels; and/or (xii) the plug is configured to move in response to rotation of the rotary member such that the plug traverses the plug channel in response to rotation of the rotary member between the first position and the second position; and/or (xiii) further comprising forming a keyway in the rotary member, wherein the keyway is configured to receive the fluid transfer device; and/or (xiv) the rotary member is configured to rotate in response to insertion and rotation of the fluid transfer device in the keyway; and/or (xv) further comprising forming a baffle in the rotary member to obstruct contact between the plug and a flow of fluid between the first connector and the second connector; and/or (xvi) the baffle extends from a periphery of the rotary member into an interior portion of the rotary member; and/or (xvii) the baffle extends from an interior portion of the rotary member toward a periphery of the rotary member; and/or (xviii) the septum comprises a position indicator disposed on a surface opposing the rotary member, the position indicator protruding from the surface of the septum; and/or (xix) the septum is configured to seal around the fluid transfer device in response to insertion of the fluid transfer device through the septum, and the septum is configured to impede fluid communication between an interior and an exterior of the implant; and/or (xx) further comprising connecting a plurality of valves; and/or (xxi) the plurality of valves are connected to each other in series, parallel, or a combination thereof, such that all or portion of the plurality of valves are in fluid communication; and/or (xxii) further comprising disposing a biocompatible tube between at least two valves to communicate a fluid between the at least two valves; and/or (xxiii).

In another embodiment disclosed is a method for performing dialysis, the method comprising: locating an implant comprising a valve comprising a housing comprising a first connector protruding from the housing to connect to a first fluid flow member and to communicate a fluid, and a second connector protruding from the housing to connect to a second fluid flow member and to communicate the fluid, a rotary member disposed in the housing, a plug disposed in the housing and connected to the rotary member, a seat arranged proximate to or disposed in the first connector to sealingly receive the plug, and a septum disposed on and in sealing contact with the housing to receive a fluid transfer device disposed in a patient, the implant further comprising: a primary flow channel disposed in the rotary member, a secondary flow channel disposed in the rotary member and in fluid communication with the primary flow channel, and a keyway disposed in the rotary member to receive the fluid transfer device; inserting the fluid transfer device through the septum; inserting the fluid transfer device in the keyway; rotating the fluid transfer device with respect to the housing; rotating the rotary member in response to rotating the fluid transfer device; and communicating a fluid in the implant to perform dialysis, wherein the rotary member is configured to rotate between a first position and second position.

In various embodiments (i) further comprising disposing the implant in the patient prior to locating the implant; and/or (ii) disposing the implant comprises: connecting the first connector to an artery of the patient, and connecting the second connector to a vein of the patient; and/or (iii) locating the implant comprises determining the orientation of the implant by locating a position indicator disposed on a surface of the septum opposing the rotary member, the position indicator protruding from the surface of the septum; and/or (iv) further comprising determining a rotational orientation of the rotary member in the housing; and/or (v) the valve further comprises a coupling to connect the plug to the rotary member; and/or (vi) the coupling is flexible and is configured to exert an outwardly radial force on the plug to urge the plug into the seat in response to the plug being proximate to the seat; and/or (vii) with the rotary member in the first position, the first connector, the second connector, the primary flow channel, and the secondary flow channel are in fluid communication; and/or (viii) the rotary member in the second position, the plug is disposed in the seat to impede fluid communication between the first connector and the second connector; and/or (ix) the rotary member further comprises a tertiary flow channel in fluid communication with the primary flow channel and the secondary flow channel; and/or (x) with the rotary member in the second position, the second connector, the primary flow channel, the secondary flow channel, and the tertiary flow channel are in fluid communication; and/or (xi) with the rotary member in the second position, the rotary member is arranged to impede fluid communication between the second connector and the primary and the secondary flow channels; and/or (xii) two plugs and two seats are present in the valve: a first seat to receive a first plug, and a second seat to receive a second plug, wherein the first seat is disposed proximate to or in the first connector, and the second seat is disposed proximate to or in the second connector; and/or (xiii) with the rotary member in the second position, the first plug is disposed in the first seat to impede fluid communication between the first connector and the primary flow channel, and the second plug is disposed in the second seat to impede fluid communication between the second connector and the primary flow channel; and/or (xiv) the rotary member further comprises a plug channel, and the plug is configured to move in response to rotation of the rotary member such that the plug traverses the plug channel in response to rotation of the rotary member between the first position and the second position; and/or (xv) the coupling comprises: a first end attached to the rotary member, a second end attached to the plug, and an intermediate portion is interposed between the first end and the second end, the intermediate portion being disposed in the plug channel; and/or (xvi) the rotary member further comprises a baffle to obstruct contact between the plug and a flow of the fluid between the first connector and the second connector; and/or (xvii) the baffle extends from a periphery of the rotary member into an interior portion of the rotary member; and/or (xviii) the baffle extends from an interior portion of the rotary member toward a periphery of the rotary member; and/or (xix) further comprising sealing the septum around the fluid transfer device in response to insertion of the fluid transfer device through the septum, wherein the septum impedes fluid communication between an interior and an exterior of the valve by the septum; and/or (xx) the first fluid flow member is an artery, and the second fluid flow member is a vein; and/or (xxi) further comprising communicating blood from the artery through the first connector, secondary flow channel, and the fluid transfer device, wherein the rotary member is in the first position to communicate blood from the artery; and/or (xxii) further comprising communicating the blood from the artery to a dialysis device, and dialyzing the blood from the artery with the dialysis device to form dialyzed blood; and/or (xxiii) further comprising communicating the dialyzed blood from the dialysis device, through the fluid transfer device, the primary flow channel, the second connector, and to the vein; and/or (xxiv) further comprising: rotating the fluid transfer device with respect to the housing, rotating the rotary member from the first position to the second position in response to rotating the fluid transfer device, and disposing the plug in the seat to impede flow from the artery; and/or (xxv) further comprising: communicating a postdialysis composition in the fluid transfer device, and disposing the postdialysis composition in the valve from the fluid transfer device; and/or (xxvi) further comprising removing the fluid transfer device from the implant; and/or (xxvii) a plurality of valves is present in the implant, such that: a first valve and second valve are disposed in the implant, a first connector of the first valve is connected to the artery, a second connector of the first valve is connected to a first connector of the second valve, and a second connector of the second valve is connected to the vein; and/or (xxviii) a plurality of fluid transfer devices is present, such that: the fluid transfer device inserted through a septum of the first valve is a first fluid transfer device, and the fluid transfer device inserted through a septum of the second valve is a second fluid transfer device; and/or (xxix) with the rotary member of each the first valve and the second valve in the first position, blood from the artery is communicated through the first fluid transfer device, and dialyzed blood is communicated from the dialysis device, through the second fluid transfer device, the primary flow channel of the second valve, the second connector of the second valve, and to the vein; and/or (xxx) the first valve and the second valve each further comprises a tertiary flow channel which is in fluid communication with the primary flow channel and the secondary flow channel; and/or (xxxi) with the rotary member of each the first valve and the second valve in the first position, fluid communication between the implant, the artery, and the vein is impeded, and the tertiary flow channel of the first valve is in fluid communication with the tertiary flow channel of the second valve; and/or (xxxii) further comprising: communicating a postdialysis composition in the first fluid transfer device, and disposing the postdialysis composition in the first valve from the first fluid transfer device, communicating the postdialysis composition from the first valve to the second valve, communicating the postdialysis composition from the second valve to the second fluid transfer device, and removing thrombolytic material, debris, a contaminant, blood, or a combination thereof from the implant; and/or (xxxiii) the implant further comprises a biocompatible tubing disposed between and interconnecting the first valve and the second valve; and/or (xxxiv) the biocompatible tube comprises an ancillary valve disposed in the biocompatible tube, the ancillary tube configured to communicate the fluid unidirectionally and otherwise impede fluid communication; and/or (xxxv) the postdialysis composition comprises an anticoagulant, saline, water, or a combination thereof.

In another embodiment a valve comprises: a housing defining a cavity having at least one connector fluidically connecting the cavity to an outside of the housing, a plug being movable within the housing at least between a first position that substantially occludes fluidic communication between the cavity and an outside of the housing through the at least one connector and a second position that allows fluidic communication between the cavity and the outside of the housing through the at least one connector, and a septum in operable communication with the housing being sealingly penetrable by a fluid transfer device, the fluid transfer device being capable of moving the plug between at least the first position and the second position. In an embodiment, the fluid transfer device is adapted for moving the plug between at least the first position and the second position, e.g., by having a non-circular shape or having a protrusion.

In various embodiments, (i) a cross sectional shape of the keyway is oval; and/or (ii) the opening is in a depression in a surface of the septum; and/or (iii) the plug moves linearly relative to the housing; and/or (iv) features on one or more components of the valve provide feedback to an operator when the plug has moved fully to at least one of the first position and the second position; and/or (v) the features also maintain the plug in the at least one of the first position and the second position when not being moved by the fluid transfer device.

While one or more embodiments have been shown and described, modifications and substitutions may be made thereto without departing from the spirit and scope of the invention. Accordingly, it is to be understood that the present invention has been described by way of illustration and not limitation. Embodiments herein can be used independently or can be combined.

All ranges disclosed herein are inclusive of the endpoints, and the endpoints are independently combinable with each other. The ranges are continuous and thus contain every value and subset thereof in the range. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A valve comprising:
    a housing defining a cavity having at least one connector fluidically connecting the cavity to an outside of the housing;
    a rotary member that is connected to a plug, the rotary member being movable within the housing at least between a first position that occludes fluidic communication between the cavity and an outside of the housing through the at least one connector, and a second position that allows fluidic communication between the cavity and the outside of the housing through the at least one connector;
    wherein the plug is located external to the rotary member to occlude the fluidic communication when the rotary member is in the first position and the plug is located in the rotary member to allow the fluidic communication when the rotary member is in the second position; and
    a septum in operable communication with the housing and being sealingly penetrable by a fluid transfer device, wherein the fluid transfer device is capable of moving the rotary member between at least the first position and the second position.

2. The valve of claim 1, wherein the at least one connector is fluidically connectable to a blood vessel, a biocompatible tube, or a combination thereof.

3. The valve of claim 1, wherein the at least one connector is a first connector and a second connector.

4. The valve of claim 3, wherein the plug occludes fluidic communication between the first and second connectors when in the first position and allows fluidic communication between the first and second connectors when in the second position.

5. The valve of claim 1, further comprising a rotor having a keyway receptive to the fluid transfer device.

6. The valve of claim 5, wherein a cross sectional shape of the keyway is noncircular.

7. The valve of claim 5, wherein a coupling connects the rotor to the plug.

8. The valve of claim 7, wherein the coupling is configured to bias the plug against a seat located proximate to the at least one connector.

9. The valve of claim 1, wherein the septum includes an opening receptive to the fluid transfer device.

10. The valve of claim 9, wherein the opening is circular.

11. The valve of claim 9, wherein the opening in the septum is able to reseal itself to fluidic communication between the cavity and an outside of the housing through the opening after removal of the fluid transfer device.

12. The valve of claim 1, wherein the septum includes a position indicator, which correlates to a position of the plug.

13. The valve of claim 1, further comprising a seat arranged proximate to the at least one connector.

14. The valve of claim 13, wherein the seat is sealingly receptive to the plug.

15. The valve of claim 14, wherein the plug fills a volume of at least an outer portion of the connector.

16. The valve of claim 1, wherein the valve is implantable within a patient's body.

17. The valve of claim 1, wherein the plug is sized and configured to fill a volume defined by the at least one connector when the plug is in the first position.

18. An implant, comprising:
    the valve of claim 1 which is implantable within a human body.

19. A method of dialysis, the method comprising:
    locating a valve disposed within a patient;
    inserting a fluid transfer device in a keyway of the valve;
    rotating the fluid transfer device with respect to a housing of the valve to open the valve; and
    communicating a fluid through the fluid transfer device to perform dialysis, wherein the valve comprises
    a housing defining a cavity having at least one connector fluidically connecting the cavity to an outside of the housing,
    a rotary member that is connected to a plug, the rotary member being movable within the housing at least between a first position that occludes fluidic communication between the cavity and an outside of the housing through the at least one connector and a second position that allows fluidic communication between the cavity and the outside of the housing through the at least one connector,
    wherein the plug is located external to the rotary member to occlude the fluidic communication when the rotary member is in the first position and the plug is located in the rotary member to allow the fluidic communication when the rotary member is in the second position; and a septum in operable communication with the housing and being sealingly penetrable by a fluid transfer device, the fluid transfer device being capable of moving the rotary member between at least the first position and the second position.

20. The method of claim 19, further comprising administering a postdialysis composition through the fluid transfer device to remove a residual fluid from the valve.

21. The method of claim 20, wherein the postdialysis composition is heparinized saline.

22. The method of claim 21, wherein the residual fluid is blood, and wherein the administering replaces the blood with the heparinized saline.

23. The method of claim 20, wherein the valve comprises a first valve connected to a vein and a second valve connected to an artery, wherein the first valve and the second valve are connected by a tube, and wherein the method further comprises administering a postdialysis composition to the first valve, the second valve, and the tube to remove the residual fluid from the first valve, the second valve, and the tube.

24. The method of claim 23, wherein the administering of the postdialysis composition comprises replacing the residual fluid with the postdialysis composition.

25. The method of claim 23, wherein the tube is a biocompatible tube.

26. The method of claim 19, further comprising rotating the fluid transfer device with respect to the housing of the valve to close the valve, wherein the rotating urges a plug of the valve to engage the at least one connector of the valve such that a volume of at least an outer portion of the connector is filled by the plug.

* * * * *